(12) United States Patent
Varanasi et al.

(10) Patent No.: US 9,528,104 B2
(45) Date of Patent: Dec. 27, 2016

(54) SYSTEM FOR SIMULTANEOUS ISOMERIZATION AND FERMENTATION OF SUGARS

(71) Applicant: The University of Toledo, Toledo, OH (US)

(72) Inventors: Sasidhar Varanasi, Toledo, OH (US); Kripa Rao, San Mateo, CA (US); Patricia Ann Relue, Toledo, OH (US); Dawei Yuan, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 13/955,270

(22) Filed: Jul. 31, 2013

(65) Prior Publication Data

US 2013/0330800 A1    Dec. 12, 2013

Related U.S. Application Data

(62) Division of application No. 12/811,288, filed as application No. PCT/US2009/030033 on Jan. 2, 2009, now Pat. No. 8,507,232.

(60) Provisional application No. 61/009,973, filed on Jan. 4, 2008.

(51) Int. Cl.
*C12N 11/00* (2006.01)
*C12N 1/18* (2006.01)
*C12P 7/06* (2006.01)

(52) U.S. Cl.
CPC ............ *C12N 11/00* (2013.01); *C12N 1/18* (2013.01); *C12P 7/06* (2013.01); *Y02E 50/17* (2013.01)

(58) Field of Classification Search
CPC .............. C12N 11/00; C12N 1/18; C12P 7/06; Y02E 50/17

USPC ............................................. 435/174, 299.1
See application file for complete search history.

(56) References Cited

U.S. PATENT DOCUMENTS

| | | | |
|---|---|---|---|
| 3,793,189 A | 2/1974 | Corbett | |
| 4,069,104 A | 1/1978 | Barker et al. | |
| 4,490,468 A | 12/1984 | Gong et al. | |
| 5,241,087 A | 8/1993 | van Eikeren | |
| 5,254,468 A * | 10/1993 | Fournier et al. | 435/162 |
| 5,397,700 A | 3/1995 | Fournier et al. | |

(Continued)

FOREIGN PATENT DOCUMENTS

WO    2005/056808 A2    6/2005

OTHER PUBLICATIONS

Altamore et al., "Cavitand Boronic Acids Mediate Highly Selective Fructose Transport", Organic Letters, 2002, vol. 4, No. 20, pp. 3489-3491.

(Continued)

*Primary Examiner* — William H Beisner
*Assistant Examiner* — Danielle Henkel
(74) *Attorney, Agent, or Firm* — MacMillan, Sobanski & Todd, LLC

(57) ABSTRACT

Methods and systems for the isomerization and fermentation of xylose and hexose sugars using an immobilized enzyme system capable of sustaining two different pH microenvironments in a single vessel are disclosed. Bilayer particles are dispersed in a mixture comprising an ionic borate source and xylose. The bilayer particles have a first region with a first enzymatic activity comprising xylose isomerase and a pH of 6 or above, and a second region having a second enzymatic activity at an acidic pH.

13 Claims, 11 Drawing Sheets

(56) References Cited

U.S. PATENT DOCUMENTS

| | | | |
|---|---|---|---|
| 5,563,069 A * | 10/1996 | Yang | 435/295.3 |
| 5,800,624 A | 9/1998 | Smith et al. | |
| 5,840,677 A | 11/1998 | Nielsen et al. | |
| 6,022,477 A * | 2/2000 | Luo et al. | 210/645 |
| 6,752,926 B2 * | 6/2004 | Christodoulatos | C02F 3/06 210/150 |
| 7,037,378 B2 | 5/2006 | Jumppanen et al. | |
| 7,674,608 B2 | 3/2010 | Varanasi et al. | |
| 8,217,211 B2 | 7/2012 | Agrawal et al. | |
| 8,507,232 B2 | 8/2013 | Varanasi et al. | |
| 8,927,240 B1 | 1/2015 | Maddi et al. | |
| 2008/0227162 A1 | 9/2008 | Varanasi et al. | |
| 2008/0248540 A1 * | 10/2008 | Yang | 435/160 |
| 2009/0011473 A1 | 1/2009 | Varanasi et al. | |
| 2009/0082604 A1 | 3/2009 | Agrawal et al. | |
| 2009/0090046 A1 | 4/2009 | O'Conner et al. | |
| 2009/0139137 A1 | 6/2009 | Ikura et al. | |
| 2009/0275098 A1 | 11/2009 | Beatty et al. | |
| 2009/0305935 A1 | 12/2009 | Cascao-Pereira et al. | |
| 2010/0004437 A1 | 1/2010 | Binder et al. | |
| 2010/0269990 A1 | 10/2010 | Dottori et al. | |
| 2010/0285552 A1 | 11/2010 | Varanasi et al. | |
| 2013/0074397 A1 | 3/2013 | Varanasi et al. | |

OTHER PUBLICATIONS

Andersson et al., "Effect of Different Carbon Sources on the Production of Succinic Acid Using Metabolically Engineered *Escherichia coli*", Biotechnology Progress, 2007, vol. 23, pp. 381-388.

Bridgwater, "Renewable Fuels and Chemicals by Thermal Processing of Biomass", Chemical Engineering Journal, 2003, vol. 91, pp. 87-102.

Byers et al., "A Feasibility Analysis of a Novel Approach for the Conversion of Xylose to Ethanol", Chemical Engineering Communications, 1992, vol. 112, No. 1, pp. 165-187, Abstract Only.

Chiang et al., "d-Xylulose Fermentation to Ethanol by *Saccharomyces cerevisiae*", Applied and Environmental Microbiology, 1981, vol. 42, No. 2, pp. 284-289.

Chiang et al., "Enzymatic and Microbial Preparation of D-Xylulose from D-Xylose", Applied and Environmental Microbiology, 1981, vol. 42, No. 1, pp. 66-69.

Dadi et al., "Enhancement of Cellulose Saccharification Kinetics Using an Ionic Liquid Pretreatment Step", Biotechnology and Bioengineering, 2006, vol. 95, No. 5, pp. 904-910, Abstract Only.

Demirbas, "Biorefineries for Biofuel Upgrading: A Critical Review", Applied Energy, 2009, vol. 86, pp. S151-S161.

Dote et al., "Recovery of Liquid Fuel From Hydrocarbon-rich Microalgae by Thermochemical Liquefaction", Fuel. 1994, vol. 73, No. 12, pp. 1855-1857.

Dukler et al., "In situ Product Removal of Ketoses by Immobilized 3-Amino Phenyl Boronic Acid: Effect of Immobilization Method on pH Profile", Biotechnology and Bioengineering, 2001, vol. 75, No. 1, pp. 25-28.

Fournier et al., "Demonstration of pH Control in a Commerial Immobilized Glucose Isomerase", Biotechnology and Bioengineering, 2000, vol. 52, No. 6, pp. 718-722, Abstract Only.

Grierson et al., "Thermal Characterisation of Microalgae under Slow Pyrolysis Conditions", Journal of Analytical and Applied Pyrolysis, 2009, vol. 85, pp. 118-123.

Inloes et al., "Ethanol Production by *Saccharomyces cerevisiae* Immobilized in Hollow-Fiber Membrane Bioreactors", Applied and Environmental Microbiology, 1983, vol. 46, No. 1, pp. 264-278.

João Miguel de Sousa André, "Mixed Matrix Membranes—A new platform for enzymatic reactions", Dissertation, 2009.

Lee et al., "Effects of Medium Components on the Growth of Anaerobiospirillum succiniciproducens and succinic acid production", Process Biochemistry, 1999, vol. 35, pp. 49-55.

Mata et al., "Microalgae for Biodiesel Production and Other Applications: A Review", Renewable and Sustainable Energy Reviews, 2009, pp. 1-16.

Miao et al., "Fast Pyrolysis of Microalgae to Produce Renewable Fuels", Journal of Analytical and Applied Pyrolysis, 2004, vol. 71, pp. 855-863.

Olivier et al., "Sugar Cane Bagasse as a Possible Source of Fermentable Carbohydrates. II. Optimization of the Xylose Isomerase Reaction for Isomerization of Xylose as well as Sugar Cane Bagasse Hydrolyzate to Xylulose in Laboratory-Scale Units", Biotechnology and Bioengineering, 1986, vol. 28, pp. 684-699.

Peng et al., "Effects of Temperature and Holding Time on Production of Renewable Fuels from Pyrolysis of Chlorella protothecoides", Journal of Applied Phycology, 2000, vol. 12, pp. 147-152.

Rao et al., "A Novel Technique that Enables Efficient Conduct of Simultaneous Isomerization and Fermentation (SIF) of Xylose", Applied Biochemistry and Biotechnology, 2008, vol. 146, pp. 101-117.

Rao et al., "Enhanced Ethanol Fermentation of Brewery Wastewater Using the Genetically Modified Strain *E. coli* KO11", Applied Microbiology and Biotechnology, 2007, vol. 74, pp. 50-60.

Ross et al., "Classification of Macroalgae as Fuel and its Thermochemical Behaviour", Bioresource Technology, 2008, vol. 99, pp. 6494-6504.

Ross et al., "Investigation of the Pyrolysis Behaviour of Brown Algae before and after Pre-treatment using PY-GC/MS and TGA", Journal of Analytical and Applied Pyrolysis, 2009, vol. 85, pp. 3-10.

Westmark et al., "Selective Monosaccharide Transport through Lipid Bilayers Using Boronic Acid Carriers", Journal of the American Chemical Society, 1996, vol. 118, pp. 11093-11100.

Wyman, "Ethanol from Lignocellulosic Biomass: Technology, Economics, and Opportunities", Bioresource Technology, 1994, vol. 50, pp. 3-16.

Yuan et al., "A Viable Method and Configuration for Fermenting Biomass Sugars to Ethanol Using Native *Saccharomyces cerevisiae*", Bioresource Technology, 2012, vol. 117, pp. 92-98.

Chinese 1st Office Action, Application No. 200980103397.4 dated Nov. 2, 2011.

PCT International Preliminary Report on Patentability, PCT/US2009/030033 filed Jan. 2, 2009, dated Jul. 15, 2010.

PCT International Search Report and the Written Opinion, PCT/US2009/030033 filed Jan. 2, 2009, dated 102 Mar. 2009.

PCT International Search Report and the Written Opinion, PCT/US2011/033030 filed Apr. 19, 2011, dated Aug. 26, 2011.

* cited by examiner

SYSTEM FOR SIMULTANEOUS ISOMERIZATION AND FERMENTATION OF SUGARS

CROSS-REFERENCE TO RELATED APPLICATIONS

This application is filed under 35 U.S.C. §111(a) as a divisional application which claims priority under 35 U.S.C. §119, 35 U.S.C. §120, and the Patent Cooperation Treaty to: parent application U.S. Ser. No. 12/811,288 filed under 35 U.S.C. §371 on Jul. 23, 2010, now U.S. Pat. No. 8,507,232 issued Aug. 13, 2013; which claims priority to PCT/US2009/030033 filed under the authority of the Patent Cooperation Treaty on Jan. 2, 2009, published; which claims priority to U.S. Provisional Application Ser. No. 61/009,973 filed under 35 U.S.C. §111(b) on Jan. 4, 2008. The disclosures of all priority applications are incorporated herein by reference in their entirety.

TECHNICAL FIELD OF THE INVENTION

The present invention generally relates to fermentation methods to produce fuel from xylose and hexose sugars.

BACKGROUND OF THE INVENTION

Ethanol is being hailed as the fuel of the future. Interest in the production of fuel ethanol from renewable sources has increased significantly. In order for fuel ethanol production to become a practical reality, cheaper substrates and more efficient production processes are needed [1, 2]. Biomass, which includes all plant and plant derived material, forms a potential renewable source of sugars that can be fermented to produce fuel ethanol and a variety of other fuels and chemicals. In addition to the many benefits common to renewable energy, biomass is particularly attractive because it is currently the only renewable sustainable energy source for liquid transportation fuel.

Lignocellulosic biomass is an attractive energy feed-stock because it is an abundant, domestic, renewable source that can be converted to liquid transportation fuels (*From Biomass to Biofuels: A Roadmap to the Energy Future*; Office of Science, US Dept. of Energy, December 2005).

Lignocellulosic biomass consists of three major components: cellulose (~40-50%), hemicellulose (~25-35%), and lignin (~15-20%) [3]. Of these, cellulose and hemicellulose constitute the polysaccharides that can be hydrolyzed to sugars that could be fermented to ethanol. In biomass, the majority of cellulose is a crystalline polymer of glucose that is relatively difficult to hydrolyze into its monomeric sugar residues. Hemicellulose is a short branched polymer of pentose and some hexose sugars that surround the cellulose fibrils and is much less organized [4]. The pentose sugars consist primarily of xylose and to a smaller extent arabinose, while the hexose sugars are usually galactose and mannose. Due to its relatively open structure, the hemicellulose fraction is easier to convert to its sugar monomers by various pretreatment techniques than the cellulose fraction.

For the conversion of lignocellulosic biomass to bioethanol to be economically feasible, it is imperative that the hemicellulose-derived monomeric sugars be fermentable along with the glucose derived from cellulose. Unfortunately, no known native (or wild type) microorganisms are able to efficiently ferment both glucose and xylose to ethanol. Wild type *Saccharomyces cerevisiae* strains can readily ferment glucose as well as other sugar components of biomass like mannose, fructose and galactose [5]. Xylose, which forms a major portion of hemicellulose, cannot be fermented by the same native strains of yeast. Several non-Saccharomyces strains of yeast, such as *Pichia stipitis* and *Candida shehatae*, are known to ferment pentose sugars more efficiently than other yeasts [6]. In such yeasts, the xylose metabolism pathway goes from xylose to xylitol to xylulose [7, 8]. In other yeast strains as well as bacteria and fungi, xylose can also be converted to xylulose via a single enzyme, xylose isomerase (XI). Several yeasts, including *S. cerevisiae*, that cannot ferment xylose are able to ferment xylulose, the ketose isomer of xylose [9-12] to ethanol. Considerable effort has been focused on the genetic modification of microorganisms so that both xylose and glucose can be efficiently metabolized using the same organism [13-25].

While genetically modified organisms (GMOs) have potential for fermentation of pentose and hexose sugars, their genetic stability, overall ethanol yield, and ability to survive under the conditions of industrial fermentation are unproven [26, 27]. Hence, an alternative approach to fermentation of xylose to ethanol involves using native yeast strains with the addition of exogenous enzymes for the isomerization of xylose. In this approach, the production of xylulose is accomplished using immobilized glucose/xylose isomerase [11, 28-30]. The appeal for this approach is that XI, along with amylase and protease, is among the most widely and cheaply available commercial enzymes [31]. Hydrolysate from lignocellulosic biomass will contain both xylose and glucose. The affinity of XI for xylose is typically 1 to 2 orders of magnitude greater than its affinity for glucose; hence, isomerization of xylose to xylulose will dominate over isomerization of glucose to fructose [31]. However, any fructose formed is readily fermentable by *Saccharomyces* to produce ethanol, so fructose formation is not a cause for concern.

Although XI is capable of converting xylose to xylulose, under conditions where XI has significant activity, the equilibrium ratio of xylose:xylulose is typically high (on the order of 5:1) [32-34]. Hence, xylose isomerization does not have a favorable forward equilibrium. One way to increase xylose conversion is to drive the isomerization forward by removal of the product xylulose. Simultaneous isomerization and fermentation (SIF), where the isomerization of xylose and the fermentation of xylulose to ethanol occur simultaneously in the same vessel, is one method for increasing xylose utilization. However, SIF does have inherent limitations due to the pH range over which XI is active. All commercially available XI's have optimal activity at pH 7 to 8, and the XI activity drops sharply as the pH decreases. In contrast, the optimal pH for the fermentation is in the range of 4 to 5. The large pH difference associated with these two steps poses a problem for conducting SIF efficiently. The SIF can be carried out at a compromised pH between 4 and 7, but the results are less than optimal for both reactions [11]. Efforts to isolate a XI with optimal activity at significantly lower pH for SIF were also noted in the literature [30]. However, it does not appear that this enzyme has the same level of activity as displayed by the commercially available enzymes.

The instant invention provides a further improvement over one of the co-inventor's prior inventions disclosed in the Fournier et al. U.S. Pat. No. 5,254,468 and the Fournier et al. U.S. Pat. No. 5,397,700, the disclosures of each of which are incorporated herein by reference in their entireties.

Considering the above-mentioned concerns, it is clear that there remains a need in the art for a method of developing a process that enables efficient fermentation of xylose and hexose sugars.

SUMMARY OF THE INVENTION

In a first broad aspect, there is provided a method of fermenting one or more sugars including xylose, comprising dispersing particles in a mixture comprising a borate source and xylose, the particles including one or more co-immobilized enzymes, and fermenting the mixture. The use of bilayer particles comprising an inner core having a first enzymatic activity and an outer region having a second enzymatic activity is further contemplated. In an embodiment of the invention, it is contemplated that the bilayer particles comprise xylose isomerase (XI) and urease.

In one embodiment of the invention is provided a method of improving a fermentation process comprising, or alternatively consisting or consisting essentially of, the following steps: i) dispersing one or more co-immobilized enzyme particles into a mixture containing a borate additive and xylose, the co-immobilized particles having an outer layer comprising urease and an inner core comprising xylose isomerase (XI) (or both of the enzymes) co-immobilized; ii) diffusing xylose from the mixture to the inner core where XI is active and xylulose formed; iii) diffusing at least a quantity of the boron, in an ionic form, from the borate additive into the inner core of, at least, some particles; iv) reacting the ionized borate with the xylulose to form an ionized borate-xylulose complex; v) migrating the ionized borate-xylulose complex to the mixture; and (vi) dissociating the ionized borate-xylulose complex in the mixture to obtain free xylulose. It is to be understood that some steps of this process may occur passively and do not require an affirmative step.

In certain embodiments, wherein the mixture has an acidic pH and at least a portion of the pellet has a different pH. Also, in certain embodiments, the pH at least a portion of the pellet is about 7 to about 8 and the pH of the mixture is about 4 to 5.5.

In certain embodiments, the mixture has an acidic pH, and an inner core of the pellet has a different pH. In certain embodiments, the pH of the inner core is about 7 to about 8 and the pH of the mixture is about 4 to about 5.5.

In certain embodiments, the borate additive comprises, or alternatively consists of, sodium tetraborate.

In certain embodiments, the ionized borate comprises, or alternatively consists of, tetrahydroxyborate ion.

In another broad aspect, there is provided a method of fermenting one or more sugars including xylose, comprising dispersing bilayer pellets in a mixture containing urea, a borate source, and a substrate, wherein the bilayer pellets comprise a porous outer region including immobilized urease and a porous inner core including an immobilized enzyme other than urease that acts on the substrate, and fermenting the mixture.

In another embodiment there is provided a method of producing a product using co-immobilized bilayer pellets having an outer layer of a porous material containing immobilized urease and an inner core of a porous material containing an immobilized enzyme other than urease that acts on a substrate to produce the product, the method comprising, or alternatively consisting of or consisting essentially of, the following steps: i) dispersing the bilayer pellets in a mixture containing urea, a borate additive, and the substrate, the mixture having an acidic pH; ii) reacting the urease with urea diffusing into the outer layer to produce ammonia, which consumes hydrogen ions diffusing toward the inner core to provide an inner core with a pH higher than the acidic pH of the mixture; iii) reacting the immobilized enzyme in the inner core with the substrate as it diffuses into the inner core to produce the product; iv) reacting the ionized borate with the product to produce an ionized borate-product complex; and v) migrating the ionized borate-product complex to the mixture, where it dissociates to release free xylulose. It is to be understood that some steps of this method may occur passively and do not require an affirmative step.

In one embodiment of this method, the immobilized enzyme in the inner core is xylose isomerase and the product is xylulose.

In another broad aspect, there is provided a method for the simultaneous isomerization and fermentation (SIF) of xylose to ethanol comprising, or alternatively consisting of or consisting essentially of, the following steps: i) immobilizing xylose isomerase in a porous polymer material so as to form a substantially spherical particle, the particle forming an inner core region of a larger pellet; ii) mixing the particles with at least water, urease, a monomer, a cross-linking agent, and a polymerization initiator so as to form an aqueous medium, the aqueous medium and particles comprising an aqueous suspension; iii) maintaining the aqueous suspension at a temperature between about 0° C. to about 4° C.; iv) adding at least toluene, chloroform, and a surfactant to the suspension so as to form an aqueous hydrophobic phase; v) agitating the hydrophobic phase under nitrogen conditions and at a temperature between about 0° C. to about 4° C. to allow polymerization of the monomer and to form a thin polymer coating containing the urease immobilized therein around the particles to form bilayered immobilized enzyme pellets; vi) mixing at least xylose feedstock, urea, and yeast cells having high ethanol productivity and ethanol tolerance so as to form a bulk liquid, the bulk liquid being placed in a closed reactor having agitation means, vii) setting and adjusting the pH of the bulk liquid so as to maintain the pH in the range of about 4.0 to about 5.5, viii) dispersing the bilayered immobilized enzyme pellets in the bulk liquid; ix) adding a borate additive to the bulk solution; x) diffusing xylose into the inner core region of the pellet; xi) isomerizing the diffused xylose to xylulose by contact with xylose isomerase immobilized in the inner core; xii) diffusing the xylulose out into the bulk liquid; xiii) providing a pH in the inner core region of about 7.0 to about 8.0 by diffusing urea into the outer layer of the pellet, whereby the urea is hydrolyzed to ammonia by the immobilized urease, the ammonia neutralizing hydrogen or positively charged ions that diffuse from the bulk liquid into the inner core region of the pellet; xiv) agitating the bilayered pellets and bulk liquid under substantially anaerobic conditions and at a temperature and for a sufficiently long period of time so as to allow the fermentation of xylulose to ethanol; and, xv) fermenting xylulose to ethanol which occurs substantially contemporaneously with the isomerization of xylose to xylulose. It is to be understood that some steps of this method may occur passively and do not require an affirmative step.

It is further to be understood that the simultaneous-isomerization-and-fermentation method described herein works with: i) porous monolayer particles wherein the enzymes xylose isomerase and urease are co-immobilized together; and ii) bilayer particles that have inner and outer layers, wherein the inner layer contains xylose isomerase and the outer layer contains urease. It is also to be understood that the term "co-immobilized" herein can refer to both embodiments. It is further to be understood that the terms particles and pellets can be used interchangeably.

In another embodiment, there is provided method for the simultaneous isomerization and fermentation of xylose to ethanol, comprising the steps of mixing xylose, urea, and yeast cells having high ethanol productivity and ethanol tolerance in a reactor to form a liquid mixture, maintaining the pH of the mixture in the range of about 4.0 to about 5.5, dispersing co-immobilized enzyme particles having at least two enzymes in the mixture, adding a borate source to the mixture, diffusing xylose into the particles, isomerizing the diffused xylose to xylulose by activity of immobilized xylose isomerase, diffusing the xylulose out into the mixture, maintaining the pH of the liquid in the particle during isomerization in the range of about 7.0 to about 8.0 by diffusing urea into the particle, whereby the urea is hydrolyzed to ammonia by immobilized urease, the ammonia neutralizing hydrogen ions that diffuse into the pellet, agitating the mixture under substantially anaerobic conditions so as to allow the fermentation of xylulose to ethanol, and fermenting xylulose to ethanol.

The use of bilayer particles comprising an inner core having a first enzymatic activity and an outer region having a second enzymatic activity is further contemplated. In an embodiment of the invention, it is contemplated that the bilayer particles comprise xylose isomerase (XI) and urease.

In another embodiment, the fermentation is conducted in a closed reactor (or fermentor) with agitation.

In certain embodiments, the particles can have a polymer coating. One non-limiting example of such coating is polyacrylamide.

In certain embodiments, the borate additive comprises, or alternatively consists of, sodium tetraborate.

In certain embodiments, the method includes one or more of the following: step $ix_a$) reacting the borate additive to produce an acid-containing boron; step $x_a$) diffusing the boron-containing acid into the pellets and reacting the xylulose with the boron-containing acid to produce a complex of xylulose and borate ion; and step $xii_a$) diffusing the xylulose and borate ion compound into the bulk liquid.

In certain embodiments, the boron-containing acid comprises, or alternatively consists of, boric acid. In certain embodiments, the borate ion comprises, or alternatively consists of, tetrahydroxyborate ion.

Further contemplated is a reaction medium comprising xylose, a borate source, and urea.

In another embodiment of the invention, the methods described herein provide high yields of xylulose from xylose isomerization and high percentages of xylulose and glucose conversion into ethanol using native S. cerevisiae.

The invention provides fermentation methods for enhancing conversion of xylose to xylulose, increasing the rate of production of ethanol, and reducing the overall time required for fermentation of both C6 and C5 sugars.

In yet another embodiment, there is provided a borate-enhanced isomerization of xylose in a co-immobilized enzyme pellet system comprising a two-pH environment system. In certain embodiments, the system includes adding borax (sodium tetraborate). In certain embodiments, the two-pH environment system includes induction of a positive shift in the xylose:xylulose equilibrium resulting from a selective complexation of xylulose to tetrahydroxyborate ions formed from borax. In certain embodiments, the system includes a substantially simultaneous isomerization and fermentation (SIF) step capable of sustaining two different pH-microenvironments in a single vessel, wherein the first pH is substantially optimal for xylose isomerization, and the second pH is substantially optimal for fermentation of xylulose. In certain embodiments, the SIF step includes co-immobilization of urease with xylose isomerase.

In another broad aspect, there is provided herein a novel configuration involving a packed bed of co-immobilized enzyme pellets that is connected in series to a porous hollow fiber membrane fermentor (HFMF). The packed bed configuration provides a fermentation beer that is free from yeast and can be easily concentrated for ethanol recovery. In addition, after the ethanol has been distilled off from the fermentation beer, the remaining aqueous solution containing buffers and borate can be recycled to upstream process units (i.e., hydrolysis/isomerization), resulting in significant cost savings in consumables. The packed bed configuration also provides a facile method for recovery and reuse of the isomerization catalyst pellets since the pellets are confined to the packed bed and do not come into direct contact with yeast. The packed bed configuration allows for a high density of yeast in the HFMF which is needed for xylulose fermentation and also allows extended use of the yeast for fermentation. Unlike traditional fermentors, the yeast is not disposed of after each batch of fermentation. The modular nature of the packed bed configuration allows for easy scale-up of the SIF process without significant capital costs.

Various objects and advantages of this invention will become further apparent to those skilled in the art from the following detailed description of the preferred embodiment(s) and the examples, when read in light of the accompanying drawings.

DETAILED DESCRIPTION OF THE PREFERRED EMBODIMENT(S)

Definitions

It is to be understood that this invention is not limited to the particular methodology, protocols, cell lines, genera, and reagents described, as such may vary. It is also to be understood that the terminology used herein is for the purpose of describing particular embodiments only, and is not intended to limit the scope of the present invention.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

Of the sugars recovered from lignocellulose, D-glucose can be readily converted into ethanol by baker's or brewer's yeast (*Saccharomyces cerevisiae*). However, xylose that is obtained by the hydrolysis of the hemicellulosic portion is not fermentable by the same species of yeasts. Xylose fermentation by native yeasts can be achieved via isomerization of xylose to its ketose isomer, xylulose. Isomerization with exogenous xylose isomerase (XI) occurs optimally at a pH of 7-8 while subsequent fermentation of xylulose to ethanol occurs at a pH of 4-5.

Methods useful for achieving isomerization and fermentation are described throughout the instant application, including those methods and processes set forth previously in the Summary of the Invention.

In a first broad aspect, there is provided a method for the efficient isomerization of xylose to xylulose by using an immobilized enzyme system capable of sustaining two different pH microenvironments in a single vessel, the systems also providing conditions suitable for the fermentation.

A two-enzyme pellet test of the method described herein shows conversion of xylose to xylulose even when the immobilized enzyme pellets are suspended in a bulk solution whose pH is sub-optimal for XI activity. The co-immobilized enzyme pellets can be useful in effectively conducting "simultaneous isomerization and fermentation" (SIF) of xylose.

In a particular embodiment, to help further shift the equilibrium in favor of xylulose formation, sodium tetraborate (borax) was added to the isomerization solution. Binding of tetrahydroxyborate ions to xylulose effectively reduces the concentration of xylulose and leads to increased xylose isomerization.

In another particular embodiment, the addition of 0.05M borax to the isomerization solution containing such co-immobilized enzyme pellets resulted in xylose to xylulose conversion as high as 86% under pH conditions that are suboptimal for XI activity. As such, the method described herein is adaptable for industrial conditions and provides significant increases in the yield of ethanol from xylose in an SIF approach.

Figure 1:
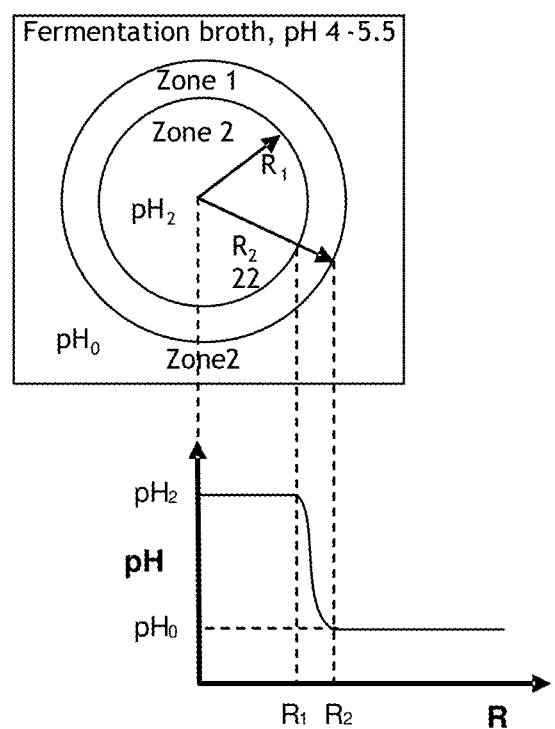
FIG. 1: Cross-section of immobilized XI, e.g. SWEETZYME™ pellet showing the steady-state pH profile developed when urease is co-immobilized in the pellet and urea is added to the fermentation broth. The pH in the fermentation broth is $pH_0$, which is typically in the range of 4 to 5. Zone 1 (outer layer) of the pellet contains immobilized urease and represents the region of the pellet where the pH changes with radial position as ammonia is produced by the consumption of urea. Zone 2 (core) represents the region of the pellet which is at $pH_2$, the elevated pH. The boundary between zones 1 and 2 represents either the point where all urea is consumed or the penetration depth of urease into the pellet.

To overcome the disparity in the optimal pH's for the isomerization and fermentation, there is now described a novel method of isomerization that incorporates urease co-immobilized with xylose isomerase. This method uses co-immobilized enzyme pellets comprising XI immobilized in a porous pellet for isomerization and the immobilized urease enzyme for pH control (FIG. 1).

When the co-immobilized enzyme pellets are dispersed in a fermentation broth which contains urea in addition to the other necessary ingredients for fermentation, it is possible to sustain a significant pH gradient between the bulk liquid and the core region of the pellet because as hydrogen ions diffuse into the pellet, they are neutralized by the ammonia produced in the hydrolysis of urea by urease. The XI, which is maintained at a higher pH in the inner core of the pellet, then catalyzes the isomerization of the xylose to xylulose; xylulose diffuses from the pellet and is then available for fermentation in the bulk solution.

Preferably, the concentration of urea used in the fermentation broth is between about 0.01 M urea and about 0.1 M urea. In a particularly preferred embodiment of the invention, the urea concentration is about 0.1 M urea.

Although the co-immobilized enzyme method is able to sustain the necessary pH difference between isomerization and fermentation steps in SIF, the overall production rate of ethanol in SIF, may be limited by the total concentration of xylulose available to the yeast. Under normal equilibrium conditions, the xylulose concentration is usually at best one fifth of the xylose concentration. Hence, there is a need for a method of shifting the equilibrium towards higher xylulose formation that will further increase the rate of ethanol production.

The method further includes the use of a borate additive in the fermentation broth, which provides a shifting of the xylose:xylulose equilibrium towards increased xylulose formation. In one embodiment of the invention, the borate additive is sodium tetraborate. In a non-limiting hypothesis of the invention, it is believe that the borate ion may shift the equilibrium between xylose and xylulose in XI catalyzed isomerization from about 20:80 to about 70:30. It is believed that the borate ion binds more tightly to xylulose than xylose, effectively reducing the product concentration, and thus shifting the equilibrium toward increased xylulose formation. This ability of borate to bind to xylulose is pH dependent, with higher pH (6 to 7.5) favoring tighter binding. Thus, as the pH increases, the concentration of free xylulose decreases. Therefore, the rate of fermentation of xylulose in the presence of borate is also pH dependent, with lower pH leading to higher free xylulose concentrations and thus higher yields and rates of ethanol production.

In certain co-immobilized enzyme methods that provide different microenvironments for isomerization and fermentation, the microenvironments can benefit by the addition of borate to the fermentation broth. Inside the co-immobilized enzyme pellet, the pH is elevated, XI is active, and the isomerization equilibrium is favored by strong borate binding to xylulose. In contrast, in the low pH fermentation broth, borate has a reduced binding affinity for xylulose, and thus produces a higher free xylulose concentration for fermentation to ethanol.

The co-immobilized enzyme method described herein is particularly effective for isomerization in conjunction with conditions optimal for fermentation by common *S. cerevisiae*. Further producers of ethanol from xylose and glucose that are useful with the invention include, but are not limited to, species of *Brettanomyces, Schizosaccharomyces, Torulaspora, Saccharomyces, Pachysolen, Kluyveromyces,* and *Hansenula*.

Conventional fermentation techniques, which are well known in the art, may be used to ferment the xylulose and glucose sugars in the bulk liquid into ethanol. As is typical in the fermentation process, largely anaerobic conditions and fermentation temperatures maintained between about 30° C. and 40° C. are useful for performing the methods and processes set forth herein, although it is to be understood that microaerophilic conditions may also be useful.

The glucose and xylose sugars may be derived from lignocellulose biomasses by conventional techniques for the hydrolysis of lignocellulose. Cellulose, which provides glucose feedstock, is difficult to hydrolyze due to its crystalline structure and close association with lignin in the biomass. In contrast, the amorphous structure of hemicellulose allows it to be easily hydrolyzed by a weak acid into its constituent sugars, namely xylose as well as arabinose and glucose.

In a particular embodiment, the media composition both shifts the equilibrium in favor of xylulose production and improves XI activity. Also, in certain embodiments, borate and/or other metal ions are useful to modulate the kinetics and/or equilibrium of the isomerization reactions. Thus, in certain embodiments, divalent metal ions are useful to increase the long-term activity of XI. In a preferred embodiment of the invention, the divalent metal ions are selected from magnesium ($Mg^{2+}$) and cobalt ($Co^{2+}$).

These advantages will now be illustrated by the following non-limiting examples. The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified.

EXAMPLES

Materials and Methods:
Chemicals:

Novo SWEETZYME™ (Sigma Aldrich G4166, ≥350 U/g with activity based on isomerization of glucose to fructose), which is immobilized glucose isomerase produced from *Streptomyces murinus*, and Genencor GENSWEET™ IGI (220 U/g with activity based on isomerization of glucose to fructose), which is immobilized glucose isomerase produced from *Streptomyces rubiginosus* was used for the isomerization of xylose. The immobilized glucose isomerase has optimal activity for glucose/fructose isomerization at pH 7.5-7.8 and 54-60° C. (as per the manufacturer). The SWEETZYME™ or GENSWEET™ pellets were dry, brown, cylinder-shaped granules with a diameter of approximately 1-3 mm Jack bean urease (Sigma U4002, 70,400 U/g) was used for generating the co-immobilized enzyme pellets used in the isomerization studies. Urease has optimal activity at pH 7.0 and 25° C. (as per manufacturer). Both enzymes were stored at 4° C. Additional chemicals, including xylose, urea, borax, magnesium chloride, cobalt chloride, sodium citrate, and Tris were all purchased from Sigma Aldrich (St. Louis, Mo.).

Immobilization of Urease on SWEETZYME™ and GENSWEET™ Pellets:

For co-immobilization of urease on the pellets, 500 ml of 1 g/l or 2 g/l urease solution and 2 g of SWEETZYME pellets were added to a 1 liter beaker. The beaker was left on the benchtop at room temperature for 24 or 48 hrs to form co-immobilized enzyme pellets.

The co-immobilized enzyme pellets were separated from the solution by decanting and gravity filtration and dried on a paper towel at room temperature for 24 hrs or until dry. The co-immobilized enzyme pellets were stored at 4° C. until use. Activity of immobilized urease was measured at pH 7.5 and 25° C. using a standard assay procedure that measures the rate of ammonia liberation. The urease activities obtained with this immobilization procedure were in the range of 550-577 U/g pellets, where a Unit liberates 1 μmol of ammonia per minute under the assay conditions.

Measurement of Xylose Isomerization Kinetics and Equilibrium:

All experiments were carried out at 34° C. in a volume of 25 ml in 50 ml shake flasks agitated at 130 rpm in an incubated shaker. Each experiment was conducted in duplicate. All experiments used 60 g/l xylose, and unless otherwise noted, 5.2 g/l of enzyme pellets (0.13 g) was used for each experiment. Buffered solutions used in making the isomerization media were 0.01 M Tris buffer (pHed to 7.5 using 0.01 M NaOH) and 0.05 M sodium citrate buffer (pHed to 4.5 using citric acid). In experiments with co-immobilized enzyme pellets, urea concentration was 0, 0.01 or 0.1 M.

Analytical Techniques and Data Analysis:

To analyze experiments for xylose and xylulose concentration, a 200 μl sample was collected at each time point. The sample was diluted 1:3 with deionized water and then filtered through a 0.2 μm filter. Xylose and xylulose calibration standards with concentrations ranging from 0.25 to 80 g/l in pH 4.5 citrate buffer were prepared in a similar manner. All standards and samples were analyzed by HPLC using a 30 μl injection volume with a 100 μl injection loop. The HPLC unit used was a Shimadzu Series 10A HPLC unit equipped with a SIL-10Ai autosampler and a refractive index detector (RID 10A). A Bio-Rad Aminex HPX-87 P (300×7.8 mm) ion exchange column was used for sugar analysis using a mobile phase of deionized water with a flow rate 0.6 ml/min and a temperature of 80° C. This column was successful in separating xylose and xylulose. To determine if the xylulose-borate complex dissociated and eluted separately, solutions of borate and borate with xylulose were injected, and the area of the borate peak was measured. Since the height of the borate peak was independent of xylulose concentration, the inventors now believe that the xylulose-borate complex dissociated into xylulose and borate, and the xylulose peak represented total xylulose in the mixture. Finally, data for xylose and xylulose concentration at each time point were summed and normalized to 60 g/l total concentration to eliminate variability and to close the mass balance. All experiments were performed in duplicate and data were very reproducible; data shown is representative of one run.

Results and Discussion:

The co-immobilized enzyme pellet system is able to achieve two different pH microenvironments within a single vessel—one optimal for XI activity and the other suitable for conducting fermentation. In addition, the sodium tetraborate decahydrate (borax) is able to alter the kinetics and shift the xylose/xylulose equilibrium.

Sustainability of Two-pH Environments in a Single Vessel Unaltered Pellets:

As an initial control experiment, the isomerization of xylose to xylulose was studied using SWEETZYME™ pellets, as received (i.e., with no co-immobilization with urease. The time course of xylose consumption and xylulose formation was monitored in a 25 ml solution for an initial xylose concentration of 60 g/l with 0.13 g pellets at 34° C. The isomerization mixture was buffered at pH 7.5, which is the optimal pH for XI activity.

Figure 2:
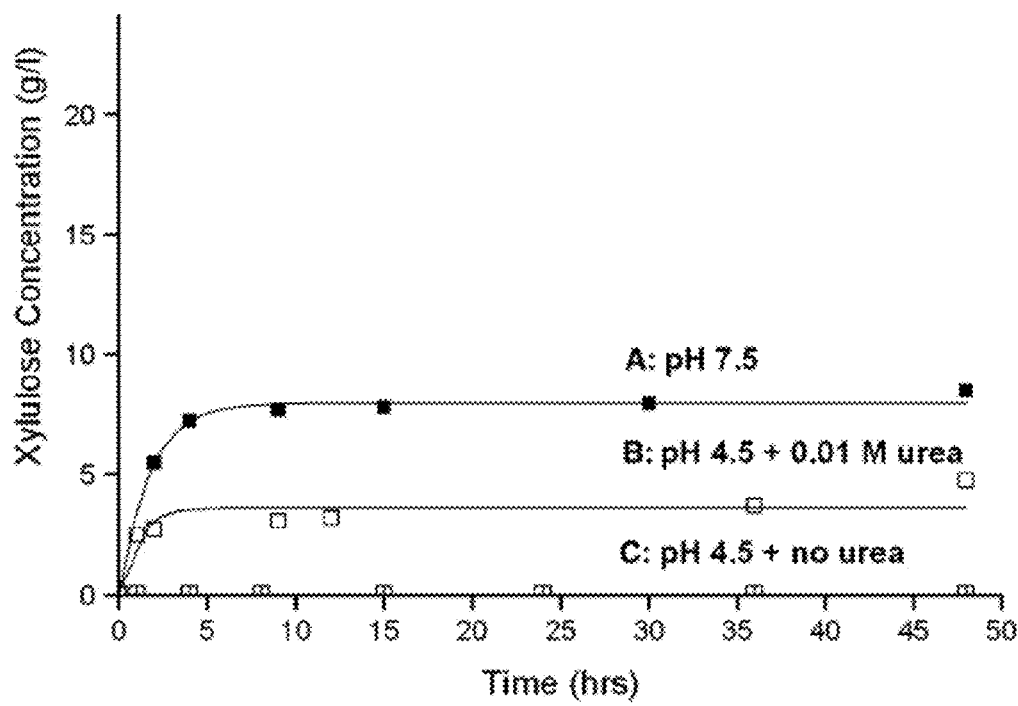
FIG. 2: Graph showing that two pH microenvironments are developed in the co-immobilized enzyme system via urea hydrolysis. Solid symbols are used for unaltered SWEETZYME™; open symbols are used for the XI/urease co-immobilized enzyme pellets. The three experiments shown are: (A) pH 7.5; (B) pH 4.5 with 0.01M urea, and (C) pH 4.5 with no urea; each used 0.13 g pellets. Unaltered SWEETZYME™ yielded no xylulose production at pH 4.5 (data not shown). Xylulose production shown for B indicates that XI has activity when urea is added. The initial xylose concentration is 60 g/l.

As seen in FIG. 2 curve A, the concentration of xylulose steadily increased and reached an equilibrium value of about 9 g/l, suggesting an equilibrium xylose:xylulose ratio of nearly 6:1 under these conditions. When the same experiment was repeated at a reduced pH of 4.5, no xylulose was detected in the reaction mixture, even after 40 hrs (data not shown). At a pH of 4.5, XI is 3 pH units below its optimum, and displays essentially no activity.

XI/Urease co-immobilized enzyme pellets:

The co-immobilized enzyme pellets were formed by adsorbing urease onto the SWEETZYME™ pellets.

The co-immobilized enzyme pellets (0.13 g) were added to 25 ml of reaction media containing 60 g/l xylose buffered to pH 4.5. As with the unaltered pellets, no xylulose formation was observed under these conditions even after 48 hrs (see FIG. 2, curve C). Next, 0.01M urea was added to the bulk solution buffered to a pH of 4.5. Formation of xylulose was observed in the presence of urea, and the concentration of xylulose in the reaction medium gradually increased to reach a value of about 5 g/l by 48 hours (see FIG. 2, curve B).

The production of ammonia by urea hydrolysis catalyzed by immobilized urease in the pellets raises the internal pH within the core of the pellets, as shown in FIG. 1. In certain embodiments, the interior pH must be well above the bulk pH of 4.5 in order for the XI within the pellets to be catalytically active. Therefore, when the xylose in the bulk solution diffuses into the pellets and reaches a higher pH region where XI is active, xylose isomerizes to form xylulose. At the same time, the continuous production of ammonia in the outer layer (Zone 1, FIG. 1) of the co-immobilized enzyme pellets also tends to neutralize any hydrogen ions that diffuse into the core of the pellets from the bulk solution, thereby sustaining the pH difference between the interior of the pellets and the external solution.

Because the rate of isomerization in curve B, shown in FIG. 2, is lower than that obtained at pH 7.5 in unaltered pellets, it shows that the interior pH is not maintained at 7.5 but at a suboptimal pH, either above or below 7.5. If the interior pH is suboptimal, then the XI activity will be lower than that in the unaltered pellets at pH 7.5, and the time required to reach equilibrium will be longer. If XI activity is reduced in the co-immobilized enzyme pellets, the time required for isomerization may ultimately exhaust the urea from the bulk solution, at which point XI activity will be lost, and the isomerization reaction will cease.

The interior pellet pH is a function of the urease loading as well as the urea concentration profile in the pellet. The Michael is constant ($K_m$) for urease hydrolysis of urea is 2.9 mM, so with 0.01 M (10 mM) urea, urea is initially being consumed at approximately 78% of $V_{max}$ at the surface of the pellet. Increasing the bulk concentration of urea results in increased ammonia production and an increase in the interior pellet pH. Depending upon whether the interior pH is above or below the pH for optimum XI activity, an increase in interior pH will decrease or increase the rate of xylose isomerization.

To achieve a desired isomerization in the co-immobilized enzyme pellet system, the urea concentration in the bulk solution can be optimized for a specific urease loading and can be maintained at a constant concentration throughout the isomerization to allow maximal, constant XI activity.

Significant XI activity in the co-immobilized enzyme pellets has been demonstrated at a bulk pH of 4.5 with 0.01M urea. Since the overall production rate of ethanol is limited by the total concentration of xylulose available to the yeast, in certain embodiments, it is desired to modify conditions to favorably enhance the isomerization and the xylose:xylulose proportions. In certain embodiments, the addition of borate to the reaction medium is used to enhance the isomerization kinetics and to favorably shift the equilibrium.

Effect of Sodium Tetraborate Addition on Xylose Isomerization

Mechanism of Sugar-Borate Complexation:

Borate leads to a shift in the equilibrium isomerization due to the binding of tetrahydroxyborate ions to aldose and ketose sugars. At near neutral pH, tetrahydroxyborate ions can be formed by hydrolysis of borax ($Na_2B_4O_5(OH)_4 \cdot 8H_2O$):

$$B_4O_5(OH)_4^{2-} + 5H_2O \leftrightarrow 3B(OH)_3 + B(OH)_4^- + OH^- \quad (1)$$

The boric acid produced in the above reaction is a weak-acid ($pK_a \sim 9$) that ionizes to a slight extent by reaction with water at neutral pH to form additional tetrahydroxyborate ions:

$$B(OH)_3 + H_2O \leftrightarrow B(OH)_4^- + H^+ \quad (2)$$

The tetrahydroxyborate ions produced in the above reactions are able to complex with adjacent hydroxyls on sugar molecules. As shown in Equations 3a and 3b, each tetrahydroxyborate ion can bind up to two molecules of sugar in a two-step process.

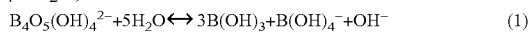
Tetrahydroxyborate ion    Sugar

Mono-complex (3b)

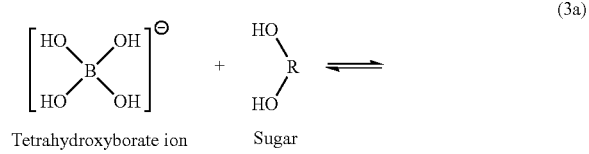
Monocomplex    Sugar

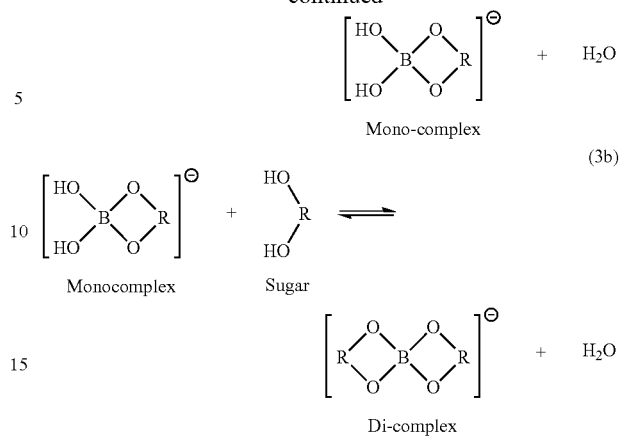
Di-complex

Borate is able to complex, via the above mechanism, more readily with the open-chain structure of xylulose as compared to the cyclic hemiacetal form of xylose. This binding preference leads to a shift in the xylose:xylulose isomerization equilibrium in favor of xylulose formation.

Figure 3:
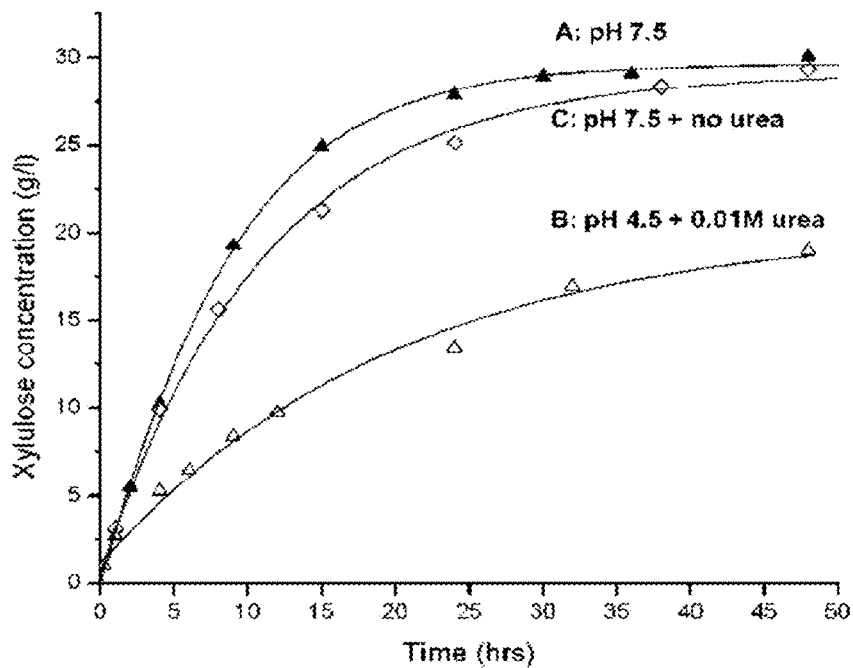
FIG. 3: Graph showing borate favorably shifts the xylose/xylulose equilibrium for both unaltered and co-immobilized enzyme pellets. Solid symbols are used for unaltered SWEETZYME™; open symbols are used for the XI/urease co-immobilized enzyme pellets. The three experiments shown are: (A) pH 7.5; (B) pH 4.5 with 0.01M urea, and (C) pH 7.5 with no urea. All three experiments show a significant shift in the equilibrium toward xylulose production. Only the conditions represented by curve B are conducive for simultaneous isomerization and fermentation. The initial xylose concentration is 60 g/l.

Unaltered Pellets: First, the effect of sodium tetraborate on the kinetics and equilibrium of isomerization for unaltered XI pellets in a buffer of pH 7.5 was studied. These data are shown in FIG. 3 curve A. When compared with the corresponding data obtained in the absence of borate (FIG. 2 curve A), even at this low concentration (0.05M) borate is able to shift the equilibrium significantly in favor of higher xylulose production. The equilibrium concentration of xylulose reaches ~30 g/l, which is more that 3 times that seen without borate (~9 g/l). Borate addition leads to an increased conversion of xylose and a shift in the equilibrium xylose:xylulose ratio from ~6:1 to ~1:1.

Urease Co-Immobilized Enzyme Pellets: The effect of urease immobilization on the pellets has a negligible impact on the overall kinetics and equilibrium achieved at pH 7.5 as shown in FIG. 3, curves A and C. (both run without urea). The immobilized urease may add a small mass transfer resistance, which could account for the slowing of the kinetics seen as the xylose concentration decreases. Next, upon adding urea (0.01M) to the citrate buffer solution, there is a significant formation of xylulose with the co-immobilized enzyme pellets, with xylulose reaching a concentration of ~17 g/l by 48 hrs. This value is much higher than the corresponding level reached without borate addition, which was about 5 g/l (see FIG. 2 curve B, and FIG. 3, curve B).

Referring again to the reactions given in Equations 1 and 2, the formation of tetrahydroxyborate ions is affected by the pH of the medium. Consequently, the ability of borax to shift the xylose:xylulose isomerization equilibrium is also a function of pH. At low pH (4 to 5) very few tetrahydroxyborate ions are formed (as the second reaction does not occur) and accordingly borax is less likely to have any influence on the isomerization equilibrium. On the other hand, in the higher pH range (6 to 8), the tetrahydroxyborate ion concentration reaches appreciable levels, and these ions bind strongly to xylulose (Eq. 3), shifting the isomerization equilibrium.

Figure 4:
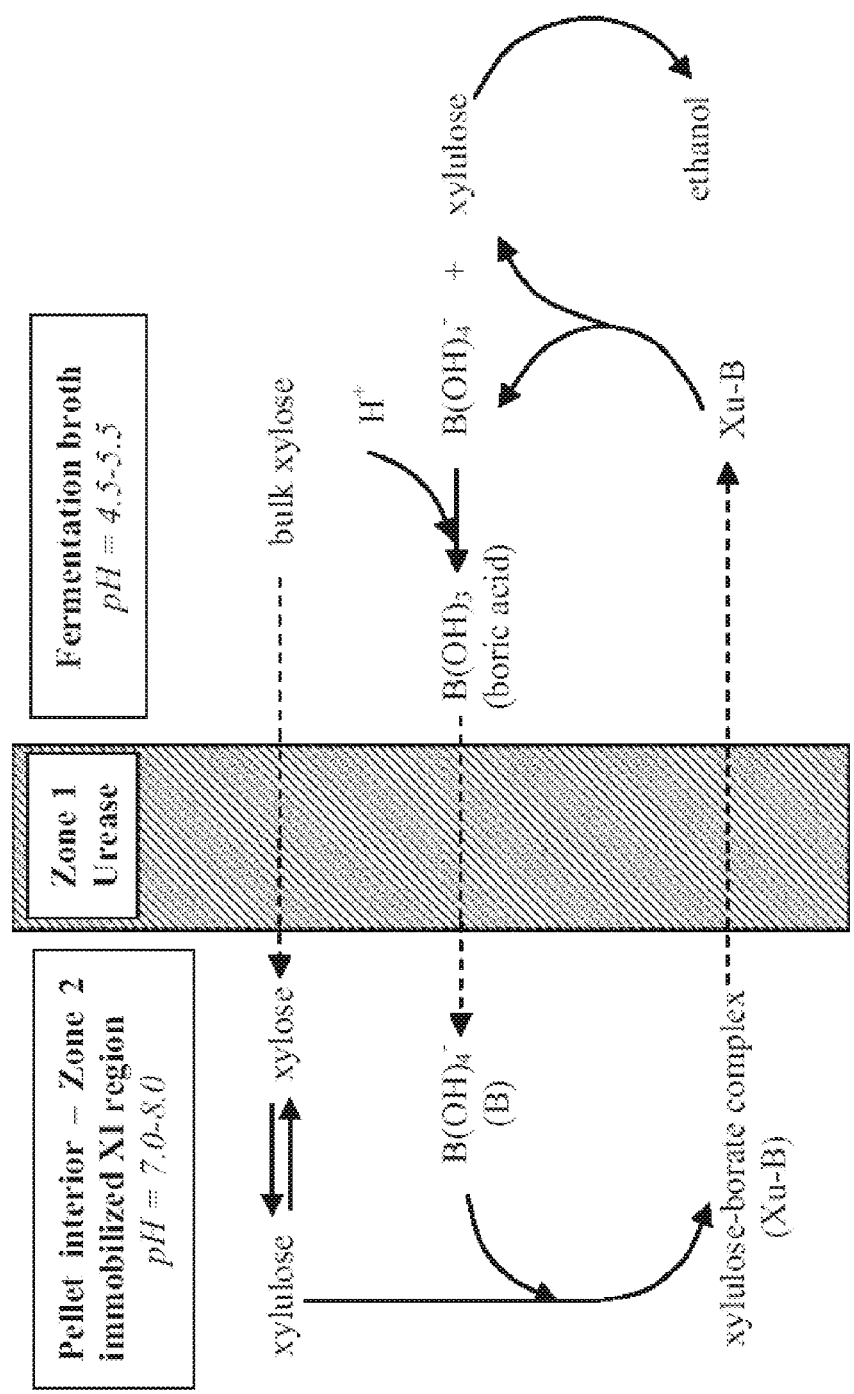
FIG. 4: Schematic illustration showing role of xylulose-borate complexation in the co-immobilized enzyme system. When sodium tetraborate (borax) is added to solution, it dissociates into tetrahydroxyborate (borate, B) ion and boric acid. In the pellet interior, higher pH favors tighter xylulose-borate binding (Xu-B complex formation), which effectively reduces the xylulose concentration in the interior and forces the isomerization forward. In the bulk, the lower pH has an uncoupling effect on the Xu-B complex, making the dissociated xylulose readily available to the yeast. Removal of xylulose via fermentation further forces dissociation of the xylulose-borate complex. Dashed lines represent transport of species; solid lines represent reactions.

As shown in FIG. 4, in the two-pH environment co-immobilized enzyme pellet system, the core region of the pellets (where the pH is high and XI is active) provides conditions conducive to strong binding of xylulose to tetrahydroxyborate ions and formation of the xylulose-borate complex (Xu-B). However, in the bulk solution where the pH is low, very little borate-sugar complex formation takes place. The likely net result of this two-pH environment in the context of SIF is that boric acid diffuses into the pellets, is converted to tetrahydroxyborate ions (Eq. 2), binds to xylulose, and ferries xylulose from inside the pellet to the bulk solution outside. In the low pH bulk solution, the Xu-B releases xylulose and the borate ions recombine with hydrogen ions to form boric acid. Thus, tetrahydroxyborate, in addition to shifting the isomerization equilibrium, facilitates the removal of xylulose from the core of the pellets into the bulk where xylulose can be readily metabolized by yeast to ethanol. Xylose feed solutions isomerized in the presence of 0.05M borate have been used in fermentation studies with yeast, and no inhibition of yeast by borate have been observed [45].

Effect of Co-Immobilized Enzyme Pellet Mass on Isomerization

The activity of the SWEETZYME™ pellets co-immobilized with urease depends on many factors. These factors include the concentration of urea and the pH in the bulk solution and the activity of urease immobilized in the outer layer (Zone 1) of the pellet. These factors influence the production of ammonia and the neutralization of the diffusing hydrogen ions, and hence the size of the active XI zone (Zone 2).

Figure 5:
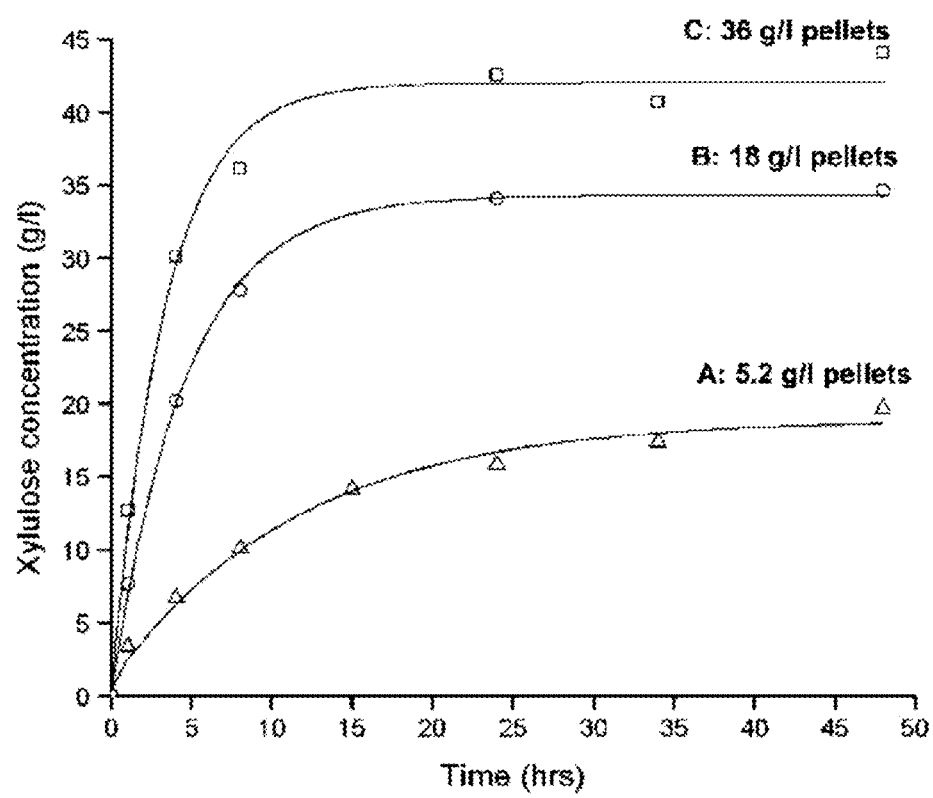
FIG. 5: Graph showing the effect of XI/urease activity on the isomerization kinetics and xylose/xylulose production for the co-immobilized enzyme pellets. All pellets were from the same co-immobilization batch and have the same urease and XI activities per g pellet at pH 7.5. The initial urea concentration used in all experiments was 0.01M. The improvement in the xylulose yields with increased enzyme loading can be attributed to the dual role of tetrahydroxyborate ions in the co-immobilized enzyme pellet system. The initial xylose concentration is 60 g/l.

In FIG. 5, transient xylulose production is shown as a function of total co-immobilized enzyme pellet mass. All pellets used were from the same co-immobilization batch and have the same urease and XI loadings. Experiments were conducted at 34° C. and pH 4.5 with 0.01M urea, 0.05M sodium tetraborate, and an initial xylose concentration of 60 g/l. Experiments shown in FIG. 5 curves B and C have 3.3 (18 g/l) and 6.6 (36 g/l) times more of each enzyme compared to curve A (5.2 g/l). At time zero in all experiments, the interior pH increases rapidly to values closer to the optimum for XI activity as ammonia is produced. In experiments B and C, the increased mass of urease and XI will cause a more rapid decrease in the bulk urea and xylose concentrations than in A. As the bulk urea concentration decreases, the ammonia production per pellet decreases and the interior pH also starts to decrease. This drop in pH occurs earlier in cases where the total urease mass (activity) is higher, leading to an accompanying loss in specific XI activity.

From the data shown in FIG. 5, the average specific XI activity was calculated for the first hour of isomerization; these results are summarized in Table 1 which shows the effect of co-immobilized enzyme pellet mass on isomerization kinetics and xylulose production. Total XI is proportional to the pellet mass, but the XI activity measured over the first hour depends on the internal pH profile within the pellet. As pellet mass increases, the bulk urea concentration decreases more rapidly and the changing internal pH profile results in an apparent decrease in specific XI activity. Although urea consumption and loss of XI activity occurs most rapidly for the highest pellet mass, the total xylulose produced while the XI is active is the greatest.

TABLE 1

| Expt | Mass Of Pellets | Ave XI Activity In First hr | Specific XI Specific Activity In First hr (Ave) | Final [Xylulose] |
|---|---|---|---|---|
| A | 0.13 g | 7.8 U | 58.5 (U/G Pellet) | 20.0 g/L |
| B | 0.45 g | 20.4 U | 45.3 (U/G Pellet) | 34.4 g/L |
| C | 0.9 g | 34.9 U | 38.8 (U/G Pellet) | 44.0 g/L |

*1 u = 1 μmol of xylulose produced per minute at 34° C. and bulk pH of 4.5.

The average specific XI activity (based on xylulose production per g of pellets at pH 4.5) decreases with increasing pellet mass. However, the corresponding total XI activity is higher, resulting in a much more rapid production of xylulose and much higher xylulose yield by 48 hrs.

The xylulose concentration (~44 g/l) at 48 hrs for the highest pellet mass is substantially higher than the value achieved (~30 gl/) with unaltered pellets at pH 7.5 with the same borate concentration (FIG. 3 curve A). For an unaltered SWEETZYME™ pellet, the kinetics of the isomerization depend on the XI activity, but the equilibrium is governed solely by the thermodynamics and is unaffected by the XI activity and pellet mass.

In the co-immobilized enzyme pellet system, there are xylulose conversions that are higher than those possible with the unaltered pellets at pH 7.5. As shown in FIG. 3 and FIG. 4, in the co-immobilized enzyme pellet system, tetrahydroxyborate acts to shift the equilibrium by binding to xylulose and also shuttles complexed xylulose from the pellet interior to the bulk solution. While not wishing to be bound by theory, the inventors herein believe that this dual role of tetrahydroxyborate is responsible for the significant improvement in xylose conversion seen in the co-immobilized enzyme pellet system when a pH gradient is established.

Figure 6:
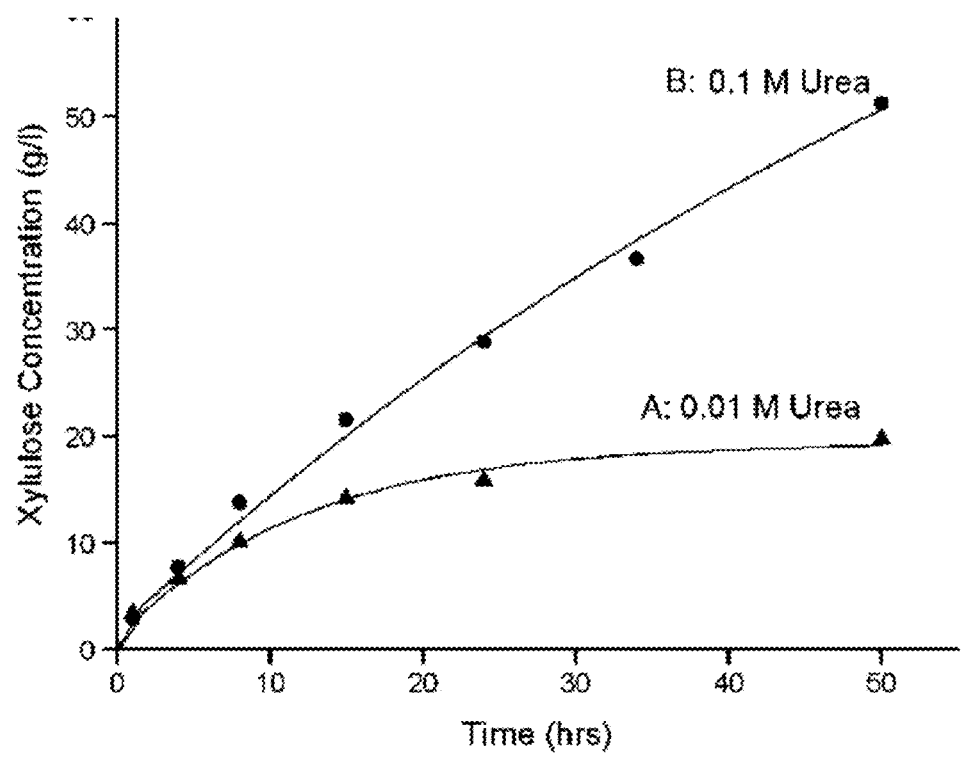
FIG. 6: Graph showing effect of initial urea concentration on the isomerization kinetics and xylulose production for the co-immobilized enzyme pellets. Both experiments use 0.13 g pellets from the same co-immobilization batch and have the same urease and XI activities per g pellet at pH 7.5. The decrease in the rate of isomerization and xylulose production seen in curve A is due to consumption of urea. In curve B, the urea concentration is high enough that the rate of xylulose isomerization does not appear to be affected by urea consumption over the entire 48 hr period. The initial xylose concentration is 60 g/l.

Effect of Urea:

The urea concentration in the bulk media will affect the rate and quantity of ammonia produced and, hence, the maintenance of the pH gradient within the co-immobilized enzyme pellet. The urea concentration will also determine the volume of the active XI core and this will, in turn, influence the kinetics of the isomerization and the extent of isomerization. In FIG. 6 transient xylulose production is shown as a function of urea concentration. All pellets used were from the same co-immobilization batch and have the same urease and XI loadings. Experiments were conducted at 34° C. and pH 4.5 with either 0.01M (FIG. 6, curve A) or 0.1M urea (FIG. 6, curve B), 0.05M sodium tetraborate, and an initial xylose concentration of 60 g/l.

As seen in these two experiments, the rate of xylose isomerization is very similar for the first 4 hours. For both cases, concentration of urea is significantly higher than the $K_m$ for urease so the internal pH profiles within the pellet are likely to be similar. Since the pellets also have the same XI loading, xylulose production is equivalent in both. However, by 8 hrs, urea consumption in FIG. 6, curve A, results in a decrease in reaction velocity for urea hydrolysis. With reduced ammonia production, the internal volume of the pellet with active XI decreases, and a drop in xylulose production relative to FIG. 6, curve B, is observed. Based on the results shown for FIG. 6, curve A, urea hydrolysis is no longer effective at maintaining the two pH microenvironments by 24 hrs. For FIG. 6, curve B, with a much higher initial urea concentration, the active zone for xylose isomerization is maintained for a much longer period of time (>48 hrs). The final xylulose concentration measured at 48 hrs was ~52 g/l, corresponding to a xylose:xylulose ratio of ~1:6.5.

Figure 7:
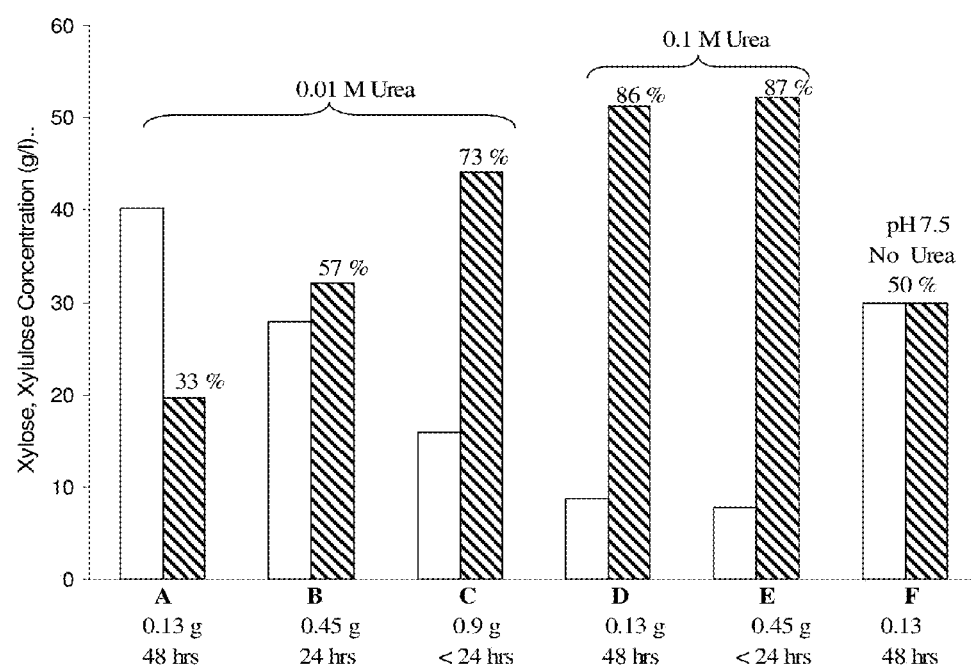
FIG. 7: Graph showing the effect of initial urea concentration and mass of pellets on xylulose production for the co-immobilized enzyme pellets. White bars are xylose; hatched bars are xylulose. All pellets (A-E) were from the same co-immobilization batch and have the same urease and XI activities per g pellet; initial pH was 4.5. Results for unaltered SWEETZYME™ are given in F. All experiments contained 0.05M borate in 25 ml of broth. The percentage of total xylulose is given above the bars for each experiment. The time of apparent equilibrium and mass of pellets used is indicated on the x axis.

Effect of Co-Immobilized Enzyme Pellet Mass on Isomerization in Presence of Excess Urea:

The effects of pellet mass and urea concentration on the final composition of the isomerization solution are summarized in FIG. 7. Pellet mass ranged from 0.13 g to 0.9 g per experiment, while the initial urea concentrations were either 0.01 or 0.1M. For 0.01M urea (FIG. 7, B and C), the increase in pellet mass results in an increase in the rate of xylulose production (see also FIG. 5) as well as an increase in the total xylulose produced. However, none of the experiments with 0.01M urea reach a xylulose yield as high as that achieved with the lowest pellet mass when 0.1M urea is added. For 0.1M urea (FIG. 7, D and E), the increase in pellet mass also results in an increase in the rate of xylulose production and a reduction in the time required to reach the final solution composition, but the final xylulose yields remain unchanged. Although increasing the pellet mass (more XI) increases the isomerization kinetics, urea plays an essential role in maintaining XI activity and achieving high xylulose yields. The co-immobilized enzyme system, by virtue of the unique two-pH microenvironments and the borate shuttling of xylulose to the bulk, results in conversion of xylose to xylulose (~86%) that is significantly higher than that achievable with the native XI at its optimal pH (FIG. 7,F).

In simultaneous-isomerization-and-fermentation (SIF) experiments, the co-immobilized enzyme pellets were added to the broth in a standard fermentor, initial isomerization was allowed for 24 hrs, and then yeast was added to initiate fermentation.

As shown in Table 2 for pure xylose, the inventors are able to ferment to 98% of the theoretical yield of ethanol in 28 hrs. To simulate hydrolysate, the inventors also fermented a sugar media containing equal amounts of glucose and xylose. These results for mixed sugars show that in SIF mode, the inventors were able to ferment nearly all of the available glucose and xylose and produce 88% ethanol yield in only 36 hrs. For the poplar hydrolysate, complete conversion of xylose is seen at the end of fermentation, indicating that SIF occurs.

TABLE 2

| Yeast | pH | T (° C.) | Time (hr) | Concentration (g/l) | | | EtOH | Yield[a] g EtOH/ g sugar | % EtOH yield |
|---|---|---|---|---|---|---|---|---|---|
| | | | | Glucose | Xylose | Xylulose | | | |
| C. shehatae NJ 23[b] | 5.5 | 30 | 48 | — | — | 50 | 17.5 | 0.350 | 68.6% |
| ATCC 2358[c] | 5 | 35 | 56 | 50 | 50 | — | 39 | 0.390 | 76.5% |
| Baker's yeast[d] - pure sugar | 5 | 34 | 28 | — | 30 | — | 15 | 0.501 | 98% |
| Baker's yeast[d] - mixed sugars | 5 | 34 | 36 | 30 | 30 | — | 27 | 0.45 | 88% |
| Baker's yeast[d] - IL-pretreated poplar hydrolysate | 5 | 34 | 24 | 9 | 4 | — | 6.5 | 0.50 | 98% |

[a]The theoretical ethanol yield is 0.51 g ethanol per g sugar.
[b]Adapted strain [1].
[c]Unaltered XI for xylose to xylulose isomerization at compromised pH [2].
[d]Data from our laboratory using co-immobilized enzyme technology. The nutrients used are: 0.3% yeast extract, 0.6% peptone, 0.17% diammonium phosphate, 4.6 mM sodium azide, 0.1M urea, 0.05M borate, and 18 g/l pellets.

Effect of Metal Ion Addition on Xylose Isomerization

In addition to evaluating the effectiveness of borate in favorably shifting the xylose to xylulose equilibrium, maintaining sustained optimal activity of XI for long time periods was also considered. The XI enzyme requires metal ions for activity, and these ions can be depleted during the isomerization. The inventors tested whether improvement in activity of XI can be realized by the addition of $Mg^{2+}$ and $Co^{2+}$ ions to the medium.

Figure 8:
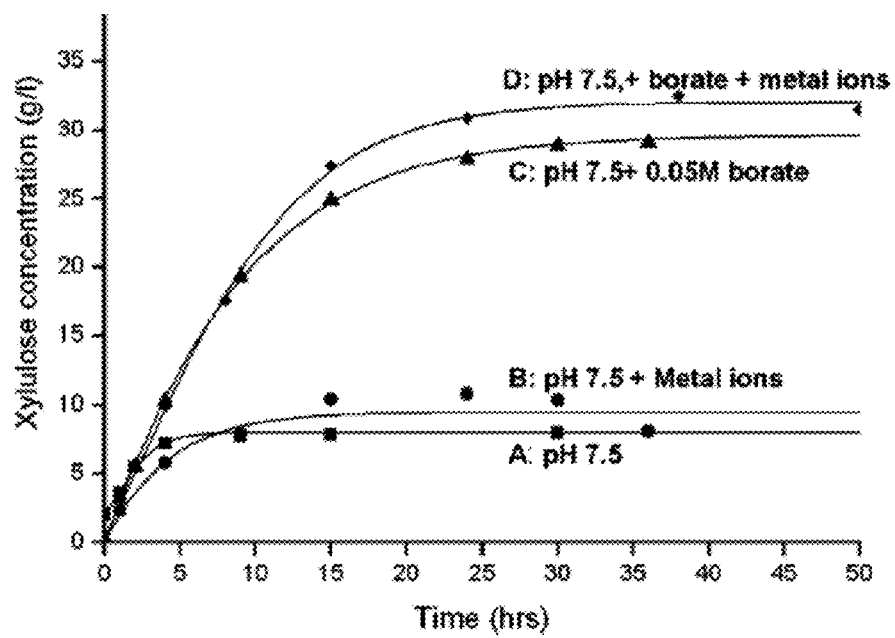
FIG. 8: Graph showing that the addition of metal ions results in a small shift in the isomerization toward xylulose, but the effect is not as significant as the shift associated with addition of sodium tetraborate. If added, sodium tetraborate was 0.05M and metal ions were 20 mM $MgCl_2$ and 1 mM $CoCl_2$. All data shown are for unaltered SWEETZYME™ at pH 7.5. The four experiments shown differ by additives and are: (A) no additives; (B) metal ions; (C) borate; and (D) borate and metal ions.

In these experiments, unaltered SWEETZYME™ at pH 7.5 was used. In the absence of borate, addition of metal ions results in a small shift in the isomerization toward xylulose (FIG. 8 curves A and B). In the presence of borate, a similar shift in the isomerization is observed (FIG. 8 curves C and D). Thus, metal ions either alone or in conjunction with borate provide an incremental improvement in the xylulose production, but the effect is not as significant as the shift associated with addition of sodium tetraborate. In certain embodiments, supplementing with metal ions may contribute to the long-term activity and reusability of the particles.

SIF of Poplar Hydrolysate with Isomerization Pellets Added to a Fermentor

When unfiltered hydrolysates are used for fermentation, the HFMF cannot be used due to plugging of the hollow fibers. SIF was conducted in three different fermentations wherein the broth contained: (1) pure xylose, (2) equal proportions of glucose and xylose, and (3) poplar hydrolysate. Borate, which was used in all experiments, did not adversely affect either the yeast viability or their ability to produce ethanol.

Figure 9:
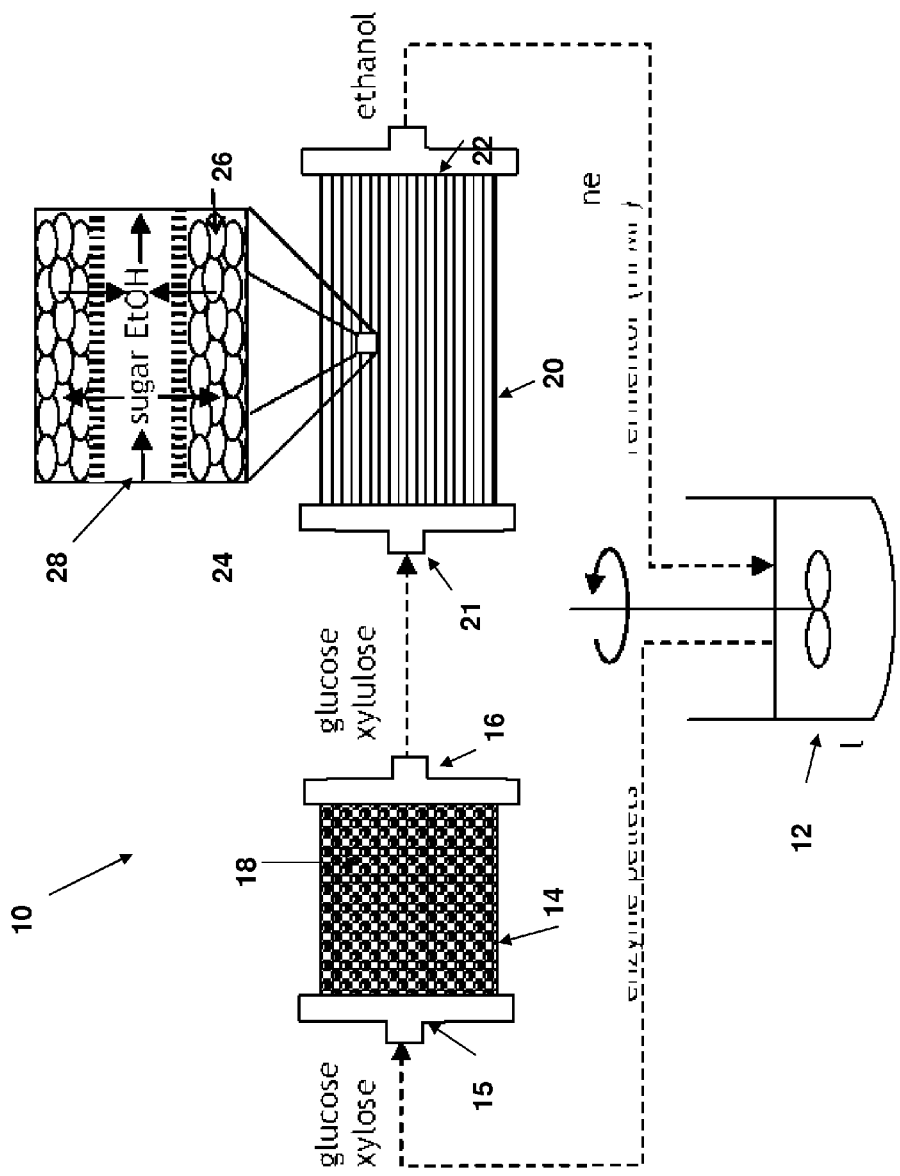
FIG. 9: Flow chart showing a packed bed and fermentor module configurations for a simultaneous isomerization and fermentation "SIF" process. The hollow fiber membrane fermentor (HFMF) shows a blow-up of a microporous fiber and yeast cells. Sugar flows through fiber lumens and yeast grow in the space surrounding the fibers. Sugars diffuse through pores in the fiber wall to yeast, where sugars are fermented to ethanol. Ethanol diffuses back through the pores into the fiber lumen and flows out of the device at the end. The yeast cells are confined to the shell space and can be loaded at a very high density per unit volume as shown.

Simultaneous-Isomerization and Fermentation (SIF) System Use with a Filtered Biomass Hydrolysate:

FIG. 9 is a schematic illustration of a packed bed of co-immobilized enzyme pellets and a fermentor module configurations for an SIF process. The hollow fiber membrane fermentor (HFMF) shows a blow-up of a microporous fiber and yeast cells. Sugar flows through fiber lumens and yeast grow in the space surrounding the fibers. Sugars diffuse through pores in the fiber wall to yeast, where sugars are fermented to ethanol. Ethanol diffuses back through the pores into the fiber lumen and flows out of the device at the end. The yeast cells are confined to the shell space and can be loaded at a very high density per unit volume as shown.

This configuration provides a fermentation beer that is free from yeast and can be easily concentrated for ethanol recovery. After the ethanol has been distilled off from the fermentation beer, the remaining aqueous solution containing buffers and borate can be recycled to the upstream process units (i.e. hydrolysis/isomerization), resulting in significant cost savings in consumables. This configuration provides a facile method for recovery and reuse of the isomerization catalyst pellets as they are confined to the packed bed and do not come into direct contact with yeast. This configuration allows for a high density of yeast in the HFMF which is needed for xylulose fermentation and also allows extended use of the yeast for fermentation. Unlike traditional fermentors, the yeast is not disposed of after each batch of fermentation. The modular nature of this configuration allows for easy scale-up of the SIF process without significant capital costs.

Use of Modular Configuration for SIF.

A packed bed reactor containing 4.5 g of urease-coated GENSWEET™ pellets was used for the isomerization of xylose. The reactor is a cylindrical column 30 cm in length with a 1 cm inner diameter (Kontes Chemistry and Life Sciences Products). An F50NRe HEMOFLOW™ hollow fiber fermentor was loaded with 50 g of dry yeast for the fermentation of the sugars to ethanol. A volume of 250 ml of a nutrient buffer containing 60 g/l glucose and 30 g/l xylose was then circulated at a rate of 30 ml/min for the isomerization and fermentation. Three different cases were run at 34° C. and pH 4.5: 1) fermentation with no pellets in the packed bed unit (no isomerization); 2) 1 hr of pre-isomerization of the sugar solution followed by simultaneous-isomerization-and-fermentation (SIF); and 3) simultaneous-isomerization-and-fermentation.

The results of these experiments are summarized in Table 3. For the three cases, all glucose is converted to ethanol within 2 hrs.

TABLE 3

| Time (Hr) | Glucose (g/l) | Xylose (g/l) | Xylulose (g/l) | Ethanol (g/l) | Ethanol Yield (g EtOH/ g sugar) | Yield (% of theoretical) |
| --- | --- | --- | --- | --- | --- | --- |
| Case 1: No isomerization | | | | | | |
| 0 | 61.98 | 30.11 | 0.00 | 0.00 | 0.00 | 0% |
| 2 | 0.00 | 17.38 | 0.00 | 29.54 | 0.40 | 78% |
| 4 | 0.00 | 16.34 | 0.00 | 30.01 | 0.40 | 78% |
| 24 | 0.00 | 14.41 | 0.00 | 30.93 | 0.40 | 78% |
| Case 2: SIF with 1 hr of pre-isomerization | | | | | | |
| 0 | 62.97 | 15.01 | 15.64 | 0.00 | 0.00 | 0% |
| 2 | 0.00 | 4.90 | 7.48 | 33.09 | 0.41 | 80% |
| 4 | 0.00 | 4.09 | 4.95 | 35.59 | 0.42 | 83% |
| 24 | 0.00 | 1.76 | 0.52 | 41.22 | 0.45 | 88% |
| Case 3: SIF | | | | | | |
| 0 | 60.20 | 30.91 | 0.00 | 0.00 | 0.00 | 0% |
| 2 | 0.00 | 18.08 | 3.05 | 31.82 | 0.45 | 89% |
| 4 | 0.00 | 18.08 | 2.88 | 34.03 | 0.49 | 95% |
| 24 | 0.00 | 14.55 | 0.00 | 37.22 | 0.49 | 95% |

In Case 1, although xylose is consumed, no ethanol is produced from this sugar as the ethanol concentration is constant between 2-24 hrs. In the absence of the xylose isomerase (XI) no xylulose is formed; the xylose is being utilized by yeast to form other metabolic products such as xylitol and arabitol.

For Case 2, half of the xylose is isomerized to xylulose prior to the initiation of fermentation. By 24 hrs, all of the glucose, all of the initial xylulose, and a fraction of the initial xylose have all been converted to ethanol. The presence of XI allows for rapid conversion of xylose to xylulose and to ethanol which reduces the flux of xylose to other byproduct pathways. These data indicate that isomerization of additional xylose and fermentation of xylulose occurs during the 24 hr period with a corresponding higher ethanol yield than for Case 1.

For Case 3, the data show that xylulose is fermented rapidly upon production as beyond 5 hrs, the concentration of xylulose is zero. However, the concentration of ethanol continues to increase and has reached 95% of the theoretical yield by 24 hrs.

Isomerization and Fermentation of a Poplar Hydrolysate in the Modular Configuration This example demonstrates the viability of the system described herein with a biomass hydrolysate. Although model sugar solutions contain the major sugars present in hydrolysate, actual hydrolysates could contain additional hydrolysis products that can be inhibitory to fermentation and isomerization. To verify how the co-immobilized enzyme pellets as well as the fermentor (HFMF) perform with actual hydrolysate, we have used a 5% w/v poplar hydrolysate prepared with a proprietary ionic liquid pretreatment method. As such, the co-pending patent application Ser. No. 11/710,357 and Ser. No. 12/075,762, are incorporated herein by reference in their entireties.

A 200 ml volume of hydrolysate was first isomerized in a packed bed containing XI pellets and then fermented in the HFMF. Isomerization was carried out with 0.05M borate for 24 hours; 91% of the xylose was isomerized to xylulose. Results of the fermentation are summarized in Table 4 which shows ethanol yield from poplar hydrolysate in an HFMF.

TABLE 4

| | Based on total fermentable sugar* | Based on fermentable sugar* consumed |
| --- | --- | --- |
| g ethanol/g sugar | 0.42 (83%) | 0.50 (98%) |

*Fermentable sugar is the sum of initial glucose and xylose before isomerization.

This combination of a packed bed of co-immobilized enzyme pellets and a hollow fiber fermentor module configurations for an SIF process has several unique and unexpected advantages: (i) it provides a fermentation beer that is free from yeast and can be easily concentrated for ethanol recovery. (ii) After the ethanol has been distilled off from the fermentation beer, the remaining aqueous solution containing buffers and borate can be recycled to the upstream process units (i.e., hydrolysis/isomerization), resulting in significant cost savings in consumables. (iii) This configuration provides a facile method for recovery and reuse of the isomerization catalyst pellets as they are confined to the packed bed and do not come into direct contact with yeast. (iv) This configuration allows for a high density of yeast in the HFMF which is needed for xylulose fermentation and also allows extended use of the yeast for fermentation. (v) Unlike traditional fermentors, the yeast is not disposed of after each batch of fermentation. (vi) The modular nature of this configuration allows for easy scale-up of the SIF process without significant capital costs.

Modular SIF Configuration for Use with Filtered Hydrolysates.

The production of cellulosic ethanol is impacted by the ability to recover lignin. In certain embodiments, it may be necessary to filtrate the hydrolysate prior to fermentation.

In another aspect, there is provided herein a modular SIF configuration that is capable of using a clarified hydrolysate. FIG. 9 shows a schematic illustration of a packed bed system 10. The modular SIF configuration allows for the easy and rapid reuse of the co-immobilized enzymes and for a flexible and efficient fermentor operation.

The packed bed system 10 includes a batch vessel 12, a packed bed column 14 having a inlet 15, an outlet 16, and containing a desired quantity of co-immobilized enzyme pellets 18, and a fermentor 20, having an inlet 21 and an outlet 22. In certain embodiments, the fermentor 20 comprises a microporous, hollow-fiber membrane 24 that separates yeast 26 from flow channels 28 in the fermentor 20.

Isomerization of xylose is conducted in the packed bed column 14 containing the immobilized enzyme pellets 18, while fermentation is conducted in the fermentor 20. The batch vessel 12, the packed bed column 14 and the fermentor 20 are connected in a closed loop system such that glucose and xylose flow into the inlet 15 of the packed bed column.

In operation, the glucose and xylose from the batch vessel 12 come into contact with the co-immobilized enzyme pellets 18 where the isomerization reaction described herein occurs. Then glucose and xylulose flow from the packed bed outlet 16 and into the fermentor inlet 21. The glucose and xylulose sugars pass through the membrane and come into contact with the yeast 26. As the yeast uses these sugars, ethanol is produced. The ethanol then passes through the membrane into the flow channel 28, and exits through the fermentor outlet 22.

By connecting the packed bed system 10 in a series configuration and by operating in a recycle mode, a "simultaneous isomerization+fermentation" SIF operation is achieved. The packed bed system 10 allows for repeated use of the pellets 18 and the fermentor 20 for a large number of batch fermentations. The packed bed system confines the yeast 26 to a shell side of the hollow fiber membrane fermentor 20 (HFMF), avoiding direct contact between the yeast and the immobilized enzyme pellets, which makes the recovery and reuse of the pellets very easy. Furthermore, in certain embodiments, the fermentor 20 has yeast densities high enough to pack the shell side such that further growth of the yeast is prevented and sugars are rapidly fermented to ethanol. The packed bed system 10 is particularly advantageous for xylulose utilization.

Figure 10:
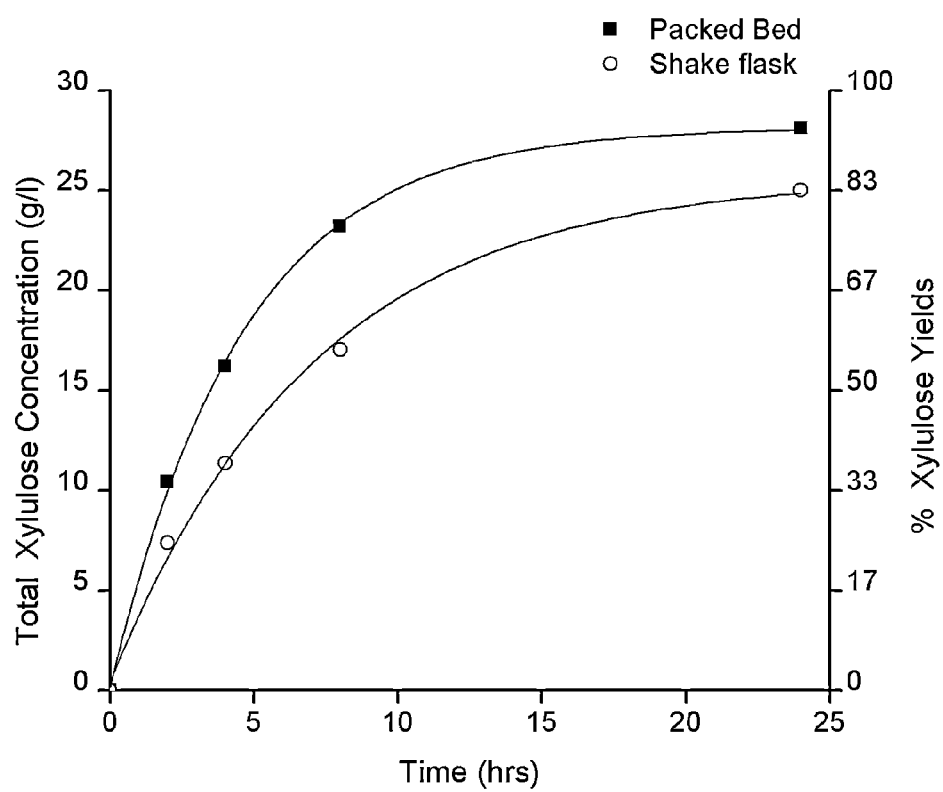
FIG. 10: Isomerization kinetics for the co-immobilized enzyme pellets in the packed bed and shake flask. All pellets were from the same co-immobilization batch and have the same urease and XI activities per g pellet at pH 7.5. The initial urea concentration used in all experiments was 0.05M. Isomerization kinetics are significantly faster for the packed bed experiment as compared to the control experiment in the agitated shake flask.
Figure 11:
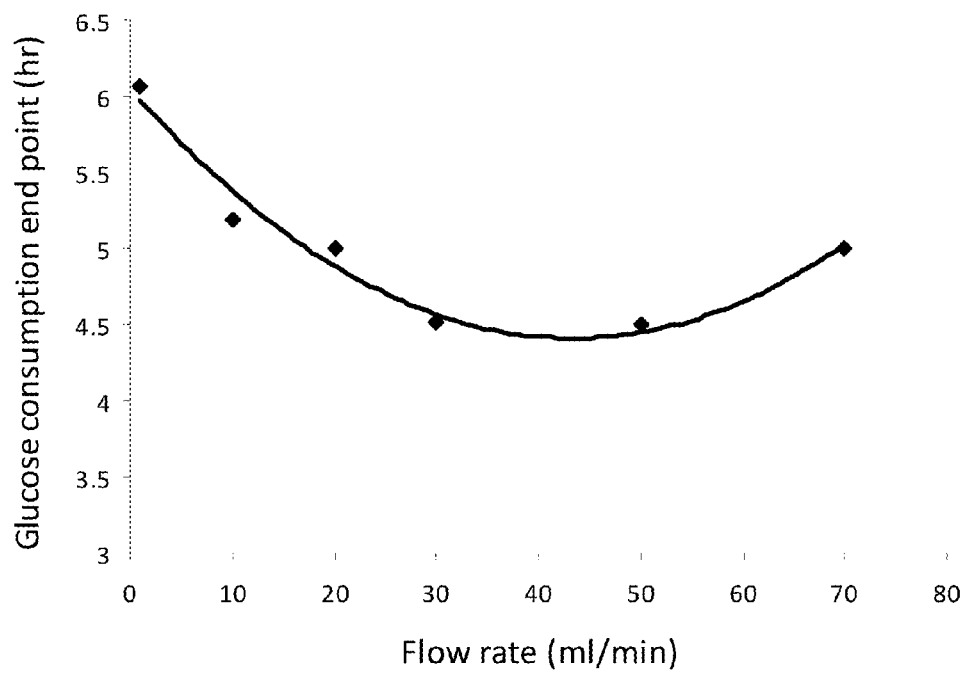
FIG. 11: Results for glucose fermentation in the HFMF. The initial glucose concentration is 60 g/l. 25 g of yeast cells were packed into the extracapillary space of the HFMF. Fermentation was conducted using different media flow rates for 24 hours. The ethanol production rate peaked at a flow of 30-50 ml/min with nearly 100% ethanol yield. The theoretical ethanol yield is 0.51 g ethanol/g glucose.

FIGS. 10 and 11 shows data for the two processes: [(1) packed bed, and (2) HFMF operated separately. For the packed bed isomerization, 0.9 g of immobilized enzyme pellets were placed in the bottom of a 5 ml glass syringe. Using a peristaltic pump, 50 ml of media containing 30 g/l xylose, 0.05 M borate and 0.05 M urea was recirculated from a reservoir through the bed at 1 ml/min while maintaining a 1 cm liquid head above the enzyme pellets in the column. The packed bed set-up was assembled in an incubator to maintain a constant temperature of 34° C. Samples were collected from the reservoir for HPLC analysis of xylose and xylulose. A control experiment with the pellets from the same immobilization batch was run in an agitated shake flask. The transient xylulose concentration and yield for the packed bed and shake flask experiments are as shown in FIG. 10. Both the rate of formation and overall yield of xylulose are higher in the packed bed, indicating that the time for isomerization may be practically reduced from ~24 hrs to less than 10 hrs due to the more efficient mass transfer of sugars to the enzymes in the packed bed design.

For the fermentation unit, a F50NR HEMOFLOW™ cartridge (Fresenius Medical Care North America) was used. The microporous fibers are made of polysulfone with a molecular weight cut-off of 25 kDa, and total membrane surface area is 1 $m^2$. A port on the shell side of the cartridge was used to introduce the yeast and to vent $CO_2$ produced during the fermentation. Yeast (Sigma YSC2-500G, 25 g) were inoculated and cultured on the shell-side (150 ml volume) of the fibers at 34° C. 250 ml of media containing 60 g/l glucose was pumped through the fiber lumens (50 ml volume) at flow rates ranging from 1-70 ml/min to determine the effect of flow rate on the ethanol fermentation rate. The concentration of ethanol was measured through a sample port off of the batch vessel.

As shown from FIG. 11, glucose was consumed within 6 hours at all flow rates, which is comparable to our batch fermentation results (data not shown). For the 30-50 ml/min range, glucose was consumed even faster than in our batch experiments, indicating that the HFMF may have a time-advantage over batch fermentation. The ethanol yield was nearly 100% for all runs, indicating minimal by-product production. These time scales are comparable to those of isomerization in the packed column, thus providing another significant advantage over the art.

It is to be understood that other sugar solutions and hydrolysates can be used to establish module sizing to minimize SIF time. Also, the modules can be scaled to accomplish larger-scale SIF. It is also to be understood that benchmarks for reusability and lifetimes for the modules can be readily established.

System for Easy and Rapid Reuse of the Co-Immobilized Enzymes for Use with Solids-Containing Hydrolysates If the pellets are added directly to a fermentation vessel with solids-containing hydrolysate, their recovery is extremely difficult. Moreover, simultaneous saccharification and fermentation (SSF) of biomass, which has several process advantages, necessitates the handling of solids-containing fermentation media.

To address the recovery and reuse of the pellets (which are a very small fraction of the residual solids) in these situations, there is also provided herein a system that allows for the easy and rapid reuse of the co-immobilized enzymes for use with solids-containing hydrolysates.

Figure 12:
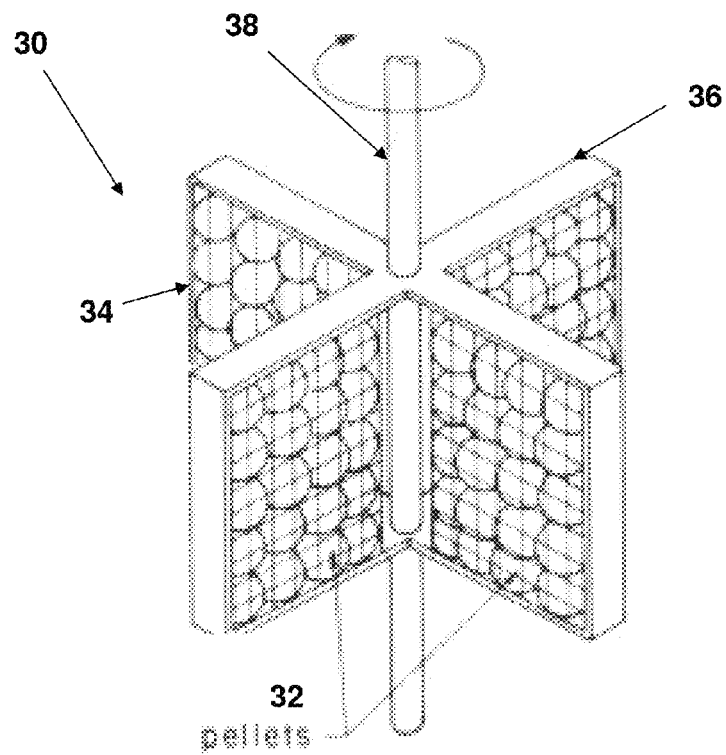
FIG. 12: Spinning basket catalytic pellet confinement that is submerged in a fermentor.

In one non-limiting example, for larger scale batch fermentations, the co-immobilized enzyme pellets can secured in a confinement system. On example of a suitable confinement system is a spinning basket system 30, as schematically illustrated in FIG. 12.

In this embodiment, the enzyme pellets 32 are packed in flat baskets 34 that form the vanes 36 of an impellor 38 that is rotated in the fermentation broth. By varying the selection of materials for the basket and by optimizing rotation speeds, attachment of solids from the fermentation broth to the baskets can be minimized. In addition, $CO_2$ generated during the fermentation will score the surfaces of the baskets, further preventing material build-up. One advantage of the spinning basket system 30 is that this confinement method is especially useful in large-scale ups in conducting heterogeneous chemical reactions.

Figure 13:
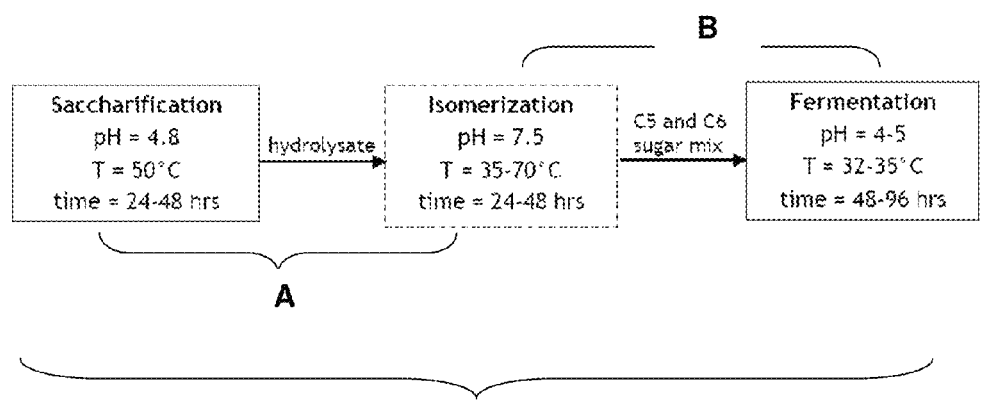
FIG. 13: Examples of process configurations using co-immobilized enzyme technology. Process A—Using co-immobilized enzyme pellets with cellulases at pH 4.8 and 50° C. in the presence of borate and urea can enable simultaneous saccharification and xylose isomerization (SSI). The resulting sugar mix of glucose and xylulose can be fermented by native yeasts. Process B—Adding co-immobilized enzyme pellets and native yeast to biomass hydrolysate at pH 4.5 and 35° C. in the presence of borate and urea allows simultaneous isomerization and fermentation (SIF) with close to theoretical ethanol yields from all biomass sugars. Process C—Simultaneous saccharification and fermentation (SSIF) of C6 and C5 sugars using native yeasts can be done with co-immobilized enzyme pellets in a medium maintained at pH 4.8 and 35° C. containing borate, urea, cellulases, and native yeast.

FIG. 13: Examples of process configurations using co-immobilized enzyme technology. Process A—Using co-immobilized enzyme pellets with cellulases at pH 4.8 and 50° C. in the presence of borate and urea can enable simultaneous saccharification and xylose isomerization (SSI). The resulting sugar mix of glucose and xylulose can be fermented by native yeasts. Process B—Adding co-immobilized enzyme pellets and native yeast to biomass hydrolysate at pH 4.5 and 35° C. in the presence of borate and urea allows simultaneous isomerization and fermentation (SIF) with close to theoretical ethanol yields from all biomass sugars. Process C—Simultaneous saccharification and fermentation (SSIF) of C6 and C5 sugars using native yeasts can be done with co-immobilized enzyme pellets in a medium maintained at pH 4.8 and 35° C. containing borate, urea, cellulases, and native yeast.

As shown in FIG. 13, cellulosic ethanol can be produced in a variety of operating configurations. Non-limiting examples include, in particular, co-immobilized enzyme pellets enable the performance of:

Process A—simultaneous saccharification and isomerization (SSI);

Process B—simultaneous isomerization and fermentation (SIF), and

Process C—simultaneous saccharification-isomerization and fermentation (SSIF).

In certain embodiments, both the enzymes XI and urease have significant activity in the temperature range of 35-70°

C. Indeed, their optimal activity is closer to 50° C., just as for the cellulases. However, unlike cellulases which have optimal activity at pH 4.8, the pH optimum for XI is 7.5. Since the methods described herein can overcome this pH discrepancy by production of the two pH microenvironments, Process A "SSI" can be conducted at elevated temperature, significantly enhancing the kinetics of isomerization and the reaction equilibrium. This results in a significant reduction in the time needed for saccharification and fermentation. Further, when the Process A includes added borate and urea to the saccharification mileau of pretreated biomass, cellulase enzyme activities are not adversely affected by these additives.

In addition, Process A ("SSI") can be implemented with a confinement system which can enable the easy recovery of the enzyme pellets following saccharification. Following Process A ("SSI"), fermentation of glucose and xylulose to ethanol can be performed in the same vessel by simply reducing the hydrolysate temperature and adding native yeast.

It is to be noted that, in certain embodiments, Process B("SIF") is especially suited to the use of bilayered pellets.

Also, in certain embodiments, with native yeasts, only the C6 sugars can be fermented to ethanol in a simultaneous-saccaraification and fermentation mode ("SSF"), while the xylose portion remains unfermented. The inability of native yeasts to ferment xylose results in a loss of nearly 40% of the available sugars from the biomass hydrolysate. Thus, the "SSF" mode may, in certain embodiments, be viable using only GMOs that can ferment both the C6 and C5 sugars of biomass at a pH of ~4.8.

As seen in FIG. 13, however, a unique feature of the co-immobilized enzyme technology is that it allows isomerization and fermentation to take place at a pH of 4.5, a pH that is also typical of enzymatic saccharification. This affords the opportunity to combine saccharification, isomerization, and fermentation all into one step. The concentration of enzyme pellets is low relative to other solids of biomass, and no significant loss of cellulases by adsorption on the particles would be expected. Also, in certain embodiments, the addition of bovine serum albumin (BSA) to the reaction medium can be done as a means of preventing loss of cellulases due to non-specific adsorption on solids other than polysaccharides.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

REFERENCES

The references discussed above and the following references, to the extent that they provide exemplary procedural or other details supplementary to those set forth herein, are specifically incorporated herein by reference. Citation of a reference herein shall not be construed as an admission that such is prior art to the present invention.

1. Zaldivar, J., Nielsen, J., and Olsson, L., *Fuel ethanol production from lignocellulose: a challenge for metabolic engineering and process integration*. Appl Microbiol Biotechnol., 56 (1-2) 2001 17-34.
2. Office of Science, U.S. D. O. E., *Breaking the Biological Barriers to Cellulosic Ethanol: A Resarch Roadmap Resulting from the Biomass to Biofuels Workshop*. December 2005, U.S Department of Energy: Rockville, Md.
3. Holtzapple, M. T., *Chapters, cellulose, hemicelluloses, and lignin.*, in *Encyclopedia of Food Science, Food Technology and Nutrition.*, M. J. Sadler, Editor. 1993, Academic Press: London. p. 758-767, 2324-2334, 2731-2738.
4. Somerville, C., Bauer, J., G., B., Facette, M., Hamann, T., Milne, J., Osborne, E., Paredez, A., Persson, S., Raab, T., Vorwerk, S., and Youngs, H., *Toward a Systems Approach to Understanding Plant Cell Walls*. Science, 306 (5705) 2004 2206-2211.
5. Van Maris, A. J. A., Abbott, D. A., Bellissimi, E., Van Den Brink, J., Kuyper, M., Luttik, M. A. H., Wisselink, H., Scheffers, A. W., Van Dijken, J. P., and Pronk, J. T., *Alcoholic fermentation of carbon sources in biomass hydrolysates by Saccharomyces cerevisiae: current status*. Antonie van Leeuwenhoek, 90 (4) 2006 391-418.
6. Prior, B. A., Kilian, S. G., and Dupreez, J. C., *Fermentation of d-xylose by the yeasts Candida shehatae and Pichia stipitis*, in *Process Biochem.* 1989. p. 21-32.
7. Tantirungkij, M., Nakashima, N., Seki, T., and Yoshida, T., *Construction of xylose-assimilating Saccharomyces cerevisiae*. Journal of Fermentation and Bioengineering, 75 (2) 1993 83-8.
8. Wang, P. Y., Shopsis, C., and Schneider, H., *Fermentation of a pentose by a yeasts*. Biochem. Biophysics. Res. Communications, 94 1980 248-254.
9. Chiang, L. C., Gong, C. S., Chen, L. F., and Tsao, G. T., *D-Xylulose Fermentation to Ethanol by Saccharomyces cerevisiae*. Applied and Environmental Microbiology, 42 (2) 1981 284-289.
10. Hsaio, H. Y., Chiang, L. C., Ueng, P. P., and Tsao, G. T., *Sequential Utilization of Mixed Monosaccharides by Yeasts*. Applied and Environmental Microbiology, 43 (4) 1982 840-845.
11. Gong, C. S., Chen, L. F., Flickinger, M. C., Chiang, L. C., and Tsao, G. T., *Production of Ethanol from D-xylose by using D-Xylose Isomerase and Yeasts*. Applied and Environmental Microbiology, 41 (2) 1981 430-436.
12. Yu, S., Jeppsson, H., and Hahn-Gaegerdal, B., *Xylulose fermentation by Saccharomyces cerevisiae and xylose fermenting yeast strains*. Applied Microbiology and Biotechnology, 44 1995 314-320.
13. Sarthy, A. V., Mcconaughy, B. L., Lobo, Z., Sundstrom, J. A., Furlong, C. E., and Hall, B. D., *Expression of the Escherichia coli xylose isomerase gene in Saccharomyces cerevisiae*. Applied and environmental microbiology, 53 (9) 1987 1996-2000.
14. Kotter, P., Amore, R., Hollenberg, C. P., and Ciriacy, M., *Isolation and characterization of the Pichia stipitis xylitol dehydrogenase gene, XYL2, and construction of a xylose-utilizing Saccharomyces cerevisiae transformant*. Current genetics, 18 (6) 1990 493-500.
15. Amore, R., Kotter, P., Kuster, C., Ciriacy, M., and Hollenberg, C. P., *Cloning and Expression in Saccharomyces cerevisiae of the NAD(P)H-dependent xylose reductase-encoding gene (XYL1) from the xylose assimilating yeast Pichia stipitis*. Gene, 109 1991 89-97

16. Moes, C. J., Pretorius, I. S., and Van Zyl, W. H., *Cloning and expression of the Clostridium thermosulfurogenes D-xylose isomerase gene (xylA) in Saccharomyces cerevisiae*. Biotechnology Letters, 18 (3) 1996 269-74.
17. Walfridsson, M., Bao, X., Anderlund, M., Lilius, G., Buelow, L., and Hahn-Gaegerdal, B., *Ethanolic fermentation of xylose with Saccharomyces cerevisiae harboring the Thermus thermophilus xylA gene, which expresses an active xylose (glucose) isomerase*. Applied and Environmental Microbiology, 62 (12) 1996 4648-4651.
18. Hahn-Hagerdal, B., Wahlbom, C. F., Gardonyi, M., Van Zyl, W. H., Otero, R. R. C., and Jonsson, L. J., *Metabolic engineering of Saccharomyces cerevisiae for xylose utilization*. Advances in Biochemical Engineering/Biotechnology, 73 (Metabolic Engineering) 2001 53-84.
19. Jeppsson, M., Johansson, B., Hahn-Gaegerdal, B., and Gorwa-Grauslund, M. F., *Reduced Oxidative Pathway flux in recombinant xylose-utilizing strains improves the ethanol yield from xylose*. Applied and Environmental Microbiology, 69 2002 5892-5897.
20. Johansson, B. and Hahn-Gaegerdal, B., *The non-oxidative pentose phosphate pathway controls the fermentation rate of xylulose, but not of xylose in Saccharomyces cerevisiae*. FEMS Yeast Research, 2 2002 277-282.
21. Verho, R., Londesborough, J., Penttilae, M., and Richard, P., *Engineering redox cofactor regeneration for improved pentose fermentation in Saccharomyces cerevisiae*. Applied and Environmental Microbiology, 69 (10) 2003 5892-5897.
22. Gardonyi, M. and Hahn-Hagerdal, B., *The Streptomyces rubiginosus xylose isomerase is misfolded when expressed in Saccharomyces cerevisiae*. Enzyme and Microbial Technology, 32 (2) 2003 252-259.
23. Kuyper, M., Harhangi, H. R., Stave, A. K., Winkler, A. A., Jetten, M. S. M., De Laat, W. T. A. M., Den Ridder, J. J. J., Op Den Camp, H. J. M., Van Dijken, J. P., and Pronk, J. T., *High-level functional expression of a fungal xylose isomerase: the key to efficient ethanolic fermentation of xylose by Saccharomyces cerevisiae?* FEMS Yeast Research, 4 (1) 2003 69-78.
24. Kuyper, M., Winkler, A. A., Van Dijken, J. P., and Pronk, J. T., *Minimal metabolic engineering of Saccharomyces cerevisiae for efficient anaerobic xylose fermentation: a proof of principle*. FEMS Yeast Research, 4 2004 655-664.
25. Kuyper, M., Toirkens, M. J., Diderich, J. A., Winkler, A. A., Van Dijken, J. P., and Pronk, J. T., *Evolutionary Engineering of mixed-sugar utilization by a xylose-fermenting Saccharomyces cerevisiae strain*. FEMS Yeast Research, 5 2005 925-934.
26. Dien, B. S., Cotta, M. A., and Jeffries, T. W., *Bacteria engineered for fuel ethanol production: current status*. Applied Microbiology and Biotechnology, 63 2003 258-266.
27. Jeffries, T. W., *Engineering yeasts for xylose metabolism*. Current Opinion in Biotechnology, 17 2006 320-326.
28. Linden, T. and Hahn-Gaegerdal, B., *Fermentation of lignocellulose hydrolysates with yeasts and xylose isomerase*. Enzyme and Microbial Technology, 11 1989 583-589.
29. Byers, J. P., Fournier, R. L., and Varanasi, S., *A Feasibility Analysis of a Novel Approach For the Conversion of Xylose to Ethanol*. Chem. Eng. Comm, 112 1992 165-187.
30. Chandrakant, P. and Bisaria, V. S., *Simultaneous bioconversion of glucose and xylose to ethanol by Saccharomyces cerevisiae in the presence of xylose isomerase*. Applied Microbiology and Biotechnology, 53 2000 301-309.
31. Bhosale, S. H., Rao, M. B., and Deshpande, V. V., *Molecular and industrial aspects of glucose isomerase*. Microbiological Reviews, 60 (2) 1996 280-300.
32. Mitsuhashi, S, and Lampen, J. O., *Conversion of D-Xylulose to D-Xylose in Extracts of Lactobacillus Pentosus*. Journal of Biological Chemistry, 204 1953 1011-1018.
33. Hochester, R. M. and Watson, R. W., *Enzymatic Isomerization of D-Xylose to D-xylulose*. Archives of Biochemistry and Biophysics, 48 1954 120-129.
34. Tewari, Y. B., Steckler, D. K., and Goldberg, R. N., *Thermodynamics of the Conversion of Aqueous Xylose to Xylulose*. Biophysical Chemistry, 22 1985 181-185.
35. Byers, J. P., Shah, M. B., Fournier, R. L., and Varanasi, S., *Generation of pH Gradient in an Immobilized Enzyme System*. Biotechnology and Bioengineering, 42 1993 410-429.
36. Fournier, R. L., Byers, J. P., Varanasi, S., and Chen, G., *Demonstration of pH Control in a Commercial Immobilized Glucose Isomerase*. Biotechnology and Bioengineering, 52 1996 718-722.
37. Boeseken, J., *The use of boric acid for the determination of the configuration of carbohydrates*. Adv Carbohydr Chem, 4 1949 189.
38. Foster, A. B., *Zone electrophoresis of carbohydrates*. Adv Carbohydr Chem, 12 1957 81.
39. Mendicino, J. F., *Effect of Borate on the Alkali-catalyzed Isomerization of Sugars*. Journal of the American Chemical Society, 82 (18) 1960 4975-4979.
40. Hsaio, H. Y., Chiang, L. C., Chen, L. F., and Tsao, G. T., *Effects of borate on isomerization and yeast fermentation of high xylulose solution and acid hydrolysate of hemicellulose*. Enzyme and Microbial Technology, 4 1982 25-31.
41. Allen, K. N., Lavie, A., Glassfeld, A., Tanada, T. N., Jenny, D. P., Carlson, S.C., Farber, G. K., Petsko, G. A., and Ringe, D., *Role of the Divalent Metal Ion in Sugar Binding, Ring Opening and Isomerization by D-Xylose Isomerase; Replacement of a catalytic metal by an amino acid*. Biochemistry, 33 1994 1488-1494.
42. Liu, H. H. and Shi, Y., *The Reaction Pathway of the Isomerization of D-Xylose Catalysed by the Enzyme D-Xylose Isomerase:A theoretical study*. Proteins: Structure, Function and Genetics, 27 1997 545-55.
43. Worthington, C. E., *Enzymatic Assay of Urease from Jack Beans (E.C.3.5.1.5)*, in Worthington Enzyme Manual. 1972, Worthington Biochemical Corporation: Freehold, N.J. p. 146-148.
44. Rizzi, G. P., *On the Effect of Tetraborate Ions in the Generation of Colored Products in Thermally Processed Glycine-Carbohydrate Solutions*. Journal of Agricultural and Food Chemistry, 55 2007 2016-2019.
45. Hsiao, H. Y., Chiang, L. C., Chen, L. F., and Tsao, G. T., *Effects of borate on isomerization and yeast fermentation of high xylulose solution and acid hydrolysate of hemicellulose*. Enzyme and Microbial Technology, 4 1982 25-31.
46. Pastinen, O., Visuri, K., Schoemaker, H. E., and Leisola, M., *Novel reactions of xylose isomerase from Streptomyces rubiginosus*. Enzyme and Microbial Technology, 25 1999 695-700.
47. Callens, M., Kersters-Hilderson, H., Van Opstal, O., and De Bruyne, C. K., *Catalytic properties of D-xylose isomerase from Streptomyces violaceoruber*. Enzyme and Microbial Technology, 8 (11) 1988 696-700.

48. Callens, M. H., Tomme, P., Kesters-Hilderson, W., Cornelis, R., Vangrysperre, W., and Debruyne, C. K., *Metal ion binding to D-xylose isomerase from Streptomyces violaceoniger.*, Biochemistry Journal, 250 1988 285-290.

49. Gong et al. U.S. Pat. No. 4,490,468.

What is claimed is:

1. A packed bed system comprising:
a packed bed enzyme column having an inlet and an outlet and comprising co-immobilized enzyme particles, the co-immobilized enzyme particles comprising a first region having a first enzymatic activity and a second region having a second enzymatic activity, wherein the co-immobilized enzyme particles are capable of sustaining two different pH microenvironments; and
a hollow fiber membrane fermentor having an inlet and an outlet and connected in series to the packed bed enzyme column, the hollow fiber membrane fermentor comprising a microporous hollow fiber membrane composed of microporous hollow fibers, wherein the microporous hollow fiber membrane has a lumen side of the microporous hollow fibers and a shell side of the microporous hollow fibers, the lumen side defining a flow channel and the shell side defining a shell space;
wherein the outlet of the packed bed enzyme column is connected directly to the inlet of the hollow fiber membrane fermentor, the inlet being connected to the lumen side of the hollow fiber membrane fermentor.

2. The system of claim 1, wherein the system contains an aqueous solution comprising borate.

3. A packed bed system comprising:
a packed bed enzyme column having an inlet and an outlet and comprising co-immobilized enzyme particles, the co-immobilized enzyme particles comprising a first region having a first enzymatic activity and a second region having a second enzymatic activity, wherein the co-immobilized enzyme particles are capable of sustaining two different pH microenvironments;
a hollow fiber membrane fermentor having an inlet and an outlet and connected in series to the packed bed enzyme column, the hollow fiber membrane fermentor comprising a microporous hollow fiber membrane composed of microporous hollow fibers, wherein the microporous hollow fiber membrane has a lumen side of the microporous fibers and a shell side of the microporous hollow fibers, the lumen side defining a flow channel and the shell side defining a shell space; and
further comprising a sugar-fermenting microorganism in the shell space, wherein the co-immobilized enzyme particles are isomerization catalyst particles that do not come into direct contact with the microorganism;
wherein the outlet of the packed bed enzyme column is connected directly to the inlet of the hollow fiber membrane fermentor, the inlet being connected to the lumen side of the hollow fiber membrane fermentor.

4. The system of claim 1, wherein the fermentor comprises a high density of sugar-fermenting microorganism confined to the shell space.

5. The system of claim 4, wherein the microorganism is reusable for multiple fermentations.

6. The system of claim 1, further comprising a batch vessel, wherein the batch vessel, the packed bed enzyme column, and the hollow fiber membrane fermentor are connected in a closed loop system.

7. The system of claim 6, wherein the batch vessel contains a mixture of glucose and xylose, and isomerization of the xylose into xylulose occurs when the mixture comes into contact with the co-immobilized enzyme particles.

8. The system of claim 1, wherein the co-immobilized enzyme particles comprise urease and xylose isomerase.

9. The system of claim 1, wherein the shell space comprises a sugar-fermenting yeast.

10. The system of claim 9, wherein the sugar-fermenting yeast comprises *Saccharomyces cerevisiae*.

11. The system of claim 1, wherein the hollow fiber membrane fermentor comprises at least one port configured to vent a gas from the shell space.

12. The system of claim 1, wherein the microporous hollow fiber membrane comprises polysulfone fibers.

13. The system of claim 1, wherein the co-immobilized enzyme particles are reusable for multiple simultaneous-isomerization-followed-by-fermentation cycles.

* * * * *